(12) United States Patent
Ashihara et al.

(10) Patent No.: US 10,624,555 B2
(45) Date of Patent: Apr. 21, 2020

(54) MYOCARDIAL ANALYSIS APPARATUS AND MYOCARDIAL EXCITATION DETECTION APPARATUS

(71) Applicants: SHIGA UNIVERSITY OF MEDICAL SCIENCE, Otsu-shi, Shiga (JP); NIHON KOHDEN CORPORATION, Shinjuku-ku, Tokyo (JP); Takeshi Tsuchiya, Kumamoto-shi, Kumamoto (JP); NATIONAL CEREBRAL AND CARDIOVASCULAR CENTER, Suita-shi, Osaka (JP)

(72) Inventors: Takashi Ashihara, Otsu (JP); Koji Takizawa, Tokyo (JP); Tatsuo Nishihara, Tokyo (JP); Nobuhiro Suzuki, Tokyo (JP); Yuuho Iwanaga, Tokyo (JP); Akio Ota, Tokyo (JP); Takeshi Tsuchiya, Kumamoto (JP); Kazuo Nakazawa, Suita (JP); Shin Inada, Suita (JP)

(73) Assignees: SHIGA UNIVERSITY OF MEDICAL SCIENCE, Shiga (JP); NIHON KOHDEN CORPORATION, Tokyo (JP); Takeshi Tsuchiya, Kumamoto (JP); NATIONAL CEREBRAL AND CARDIOVASCULAR CENTER, Osaka (JP)

(*) Notice: Subject to any disclaimer, the term of this patent is extended or adjusted under 35 U.S.C. 154(b) by 195 days.

(21) Appl. No.: 15/561,652

(22) PCT Filed: Mar. 15, 2016

(86) PCT No.: PCT/JP2016/058124
§ 371 (c)(1),
(2) Date: Sep. 26, 2017

(87) PCT Pub. No.: WO2016/158379
PCT Pub. Date: Oct. 6, 2016

(65) Prior Publication Data
US 2018/0070844 A1 Mar. 15, 2018

(30) Foreign Application Priority Data
Mar. 30, 2015 (JP) .................................. 2015-070249

(51) Int. Cl.
*A61B 5/046* (2006.01)
*A61B 5/0402* (2006.01)
(Continued)

(52) U.S. Cl.
CPC ............ *A61B 5/046* (2013.01); *A61B 5/0402* (2013.01); *A61B 5/0408* (2013.01);
(Continued)

(58) Field of Classification Search
CPC ............................... A61B 5/046; A61B 5/0402
(Continued)

(56) References Cited

U.S. PATENT DOCUMENTS

2011/0251505 A1 10/2011 Narayan et al.
2014/0088395 A1 3/2014 Dubois et al.
(Continued)

FOREIGN PATENT DOCUMENTS

| JP | 2013523344 A | 6/2013 |
|---|---|---|
| WO | 2011127211 A2 | 10/2011 |
| WO | 2014/047405 A1 | 3/2014 |

OTHER PUBLICATIONS

Communication dated Oct. 29, 2018, issued by the European Patent Office in counterpart European Application No. 16772262.8.
(Continued)

*Primary Examiner* — Nadia A Mahmood
(74) *Attorney, Agent, or Firm* — Sughrue Mion, PLLC

(57) ABSTRACT

A myocardial excitation complementation/visualization apparatus includes an acquiring section that acquires intrac-
(Continued)

ardiac electrocardiograms of a subject, the intracardiac electrocardiograms being recorded by a recording unit having a plurality of electrodes, a processing section that performs a computation for completing and visualizing a state of excitation in a myocardium of the subject based on the intracardiac electrocardiograms, and a displaying section that displays the state of excitation in the myocardium of the subject based on an output of the processing section. The processing section includes a first generating section, a correcting section, a second generating section, and a third generating section. The displaying section displays a change of the state of excitation in the myocardium of the subject based on the visualized data.

18 Claims, 24 Drawing Sheets

(51) Int. Cl.
*A61B 5/0452* (2006.01)
*A61B 5/0408* (2006.01)
*A61B 5/0456* (2006.01)
*A61B 5/00* (2006.01)
*A61B 5/02* (2006.01)
*A61B 18/14* (2006.01)

(52) U.S. Cl.
CPC .......... *A61B 5/0452* (2013.01); *A61B 5/0456* (2013.01); *A61B 5/743* (2013.01); *A61B 5/0006* (2013.01); *A61B 5/02* (2013.01); *A61B 5/04023* (2013.01); *A61B 18/1492* (2013.01)

(58) Field of Classification Search
USPC ......................................................... 600/509
See application file for complete search history.

(56) References Cited

U.S. PATENT DOCUMENTS

| | | |
|---|---|---|
| 2014/0114204 A1 | 4/2014 | Narayan et al. |
| 2014/0213922 A1 | 7/2014 | Narayan et al. |
| 2014/0276152 A1 | 9/2014 | Narayan et al. |
| 2014/0371613 A1 | 12/2014 | Narayan et al. |
| 2015/0289807 A1 | 10/2015 | Narayan et al. |
| 2016/0095531 A1 | 4/2016 | Narayan et al. |

OTHER PUBLICATIONS

Piotrowski, Z. and Rozanowski K., "Robust Algorithm for Heart Rate (HR) Detection and Heart Rate Variability (HRV) Estimation", Jul. 1, 2010, Acta Physica Polonica: Series A, vol. 118, No. 1, 6 pages total.

Umapathy Karthikeyan et al: "Phase Mapping of Cardiac Fibrillation", Circ Arrhythm Electrophysiol, Feb. 2010, vol. 3, Issue 1, p. 105-114, (17 pages total).

Gray Richard A. et al: "Spatial and temporal organization during cardiac fibrillation", Nature, May 14, 1998, vol. 393, p. 75-78, (5 pages total).

International Search Report dated May 31, 2016, by the International Searching Authority in counterpart International Application No. PCT/JP2016/058124 (PCT/ISA/210).

Written Opinion dated May 31, 2016, by the International Searching Authority in counterpart International Application No. PCT/JP2016/058124 (PCT/ISA/237).

Written Opinion of the International Preliminary Examining Authority dated Apr. 25, 2017, by the International Preliminary Examining Authority in counterpart International Application No. PCT/JP2016/058124 (PCT/IPEA/408).

International Preliminary Report on Patentability dated Jul. 18, 2017 by the International Preliminary Examining Authority in counterpart International Application No. PCT/JP2016/058124 (PCT/IPEA/416 & PCT/IPEA/409).

Communication dated Mar. 15, 2019, issued by the European Patent Office in counterpart European Application No. 16772262.8.

International Preliminary Report on Patentability Chapter II dated Mar. 15, 2016, issued by the International Searching Authority in counterpart International Application No. PCT/JP2016/058124 (PCT/IPEA/409).

Communication dated Aug. 20, 2019, issued by the Japanese Patent Office in counterpart Japanese Application No. 2017-509521.

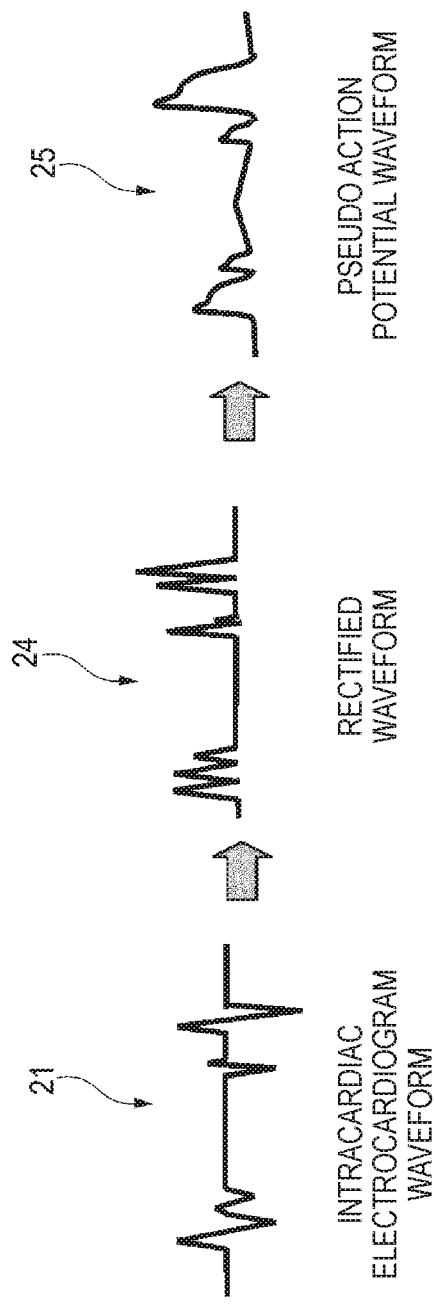
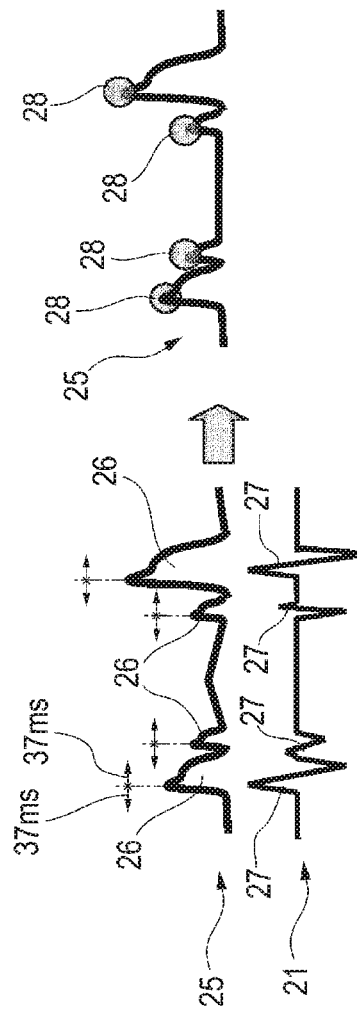
FIG. 4A
FIG. 4B

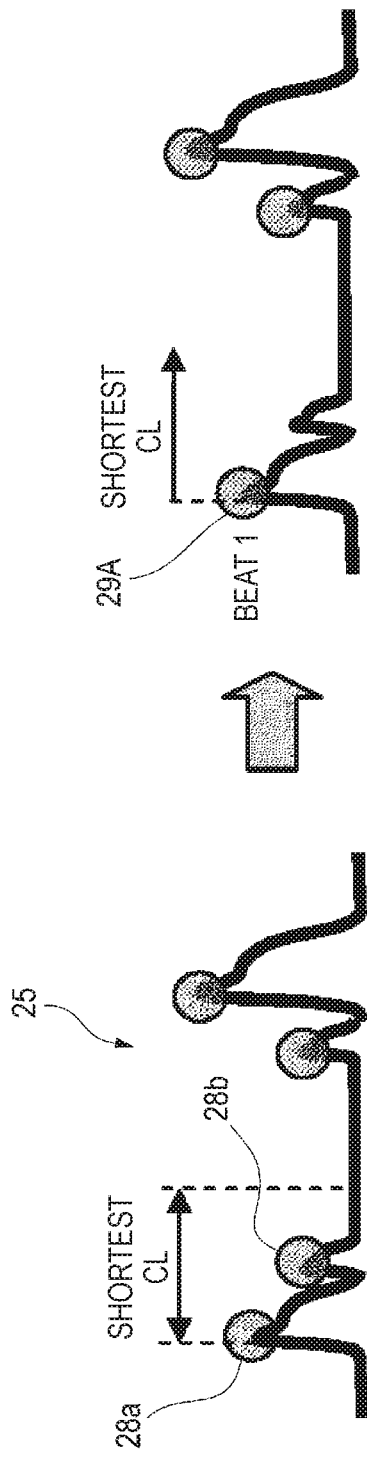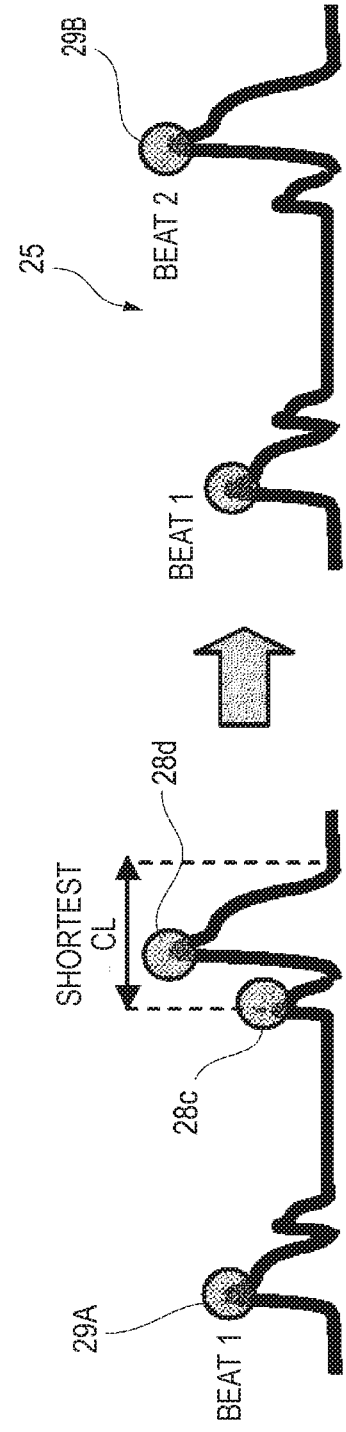

FIG. 18
SAMPLE 1
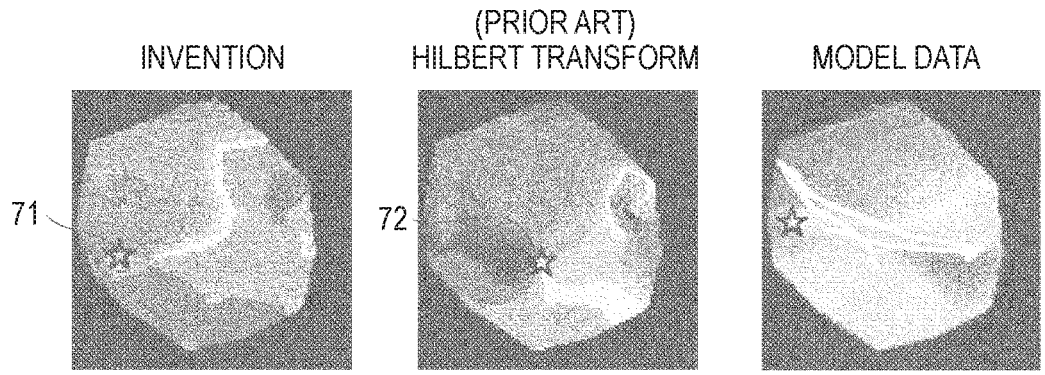
SAMPLE 2
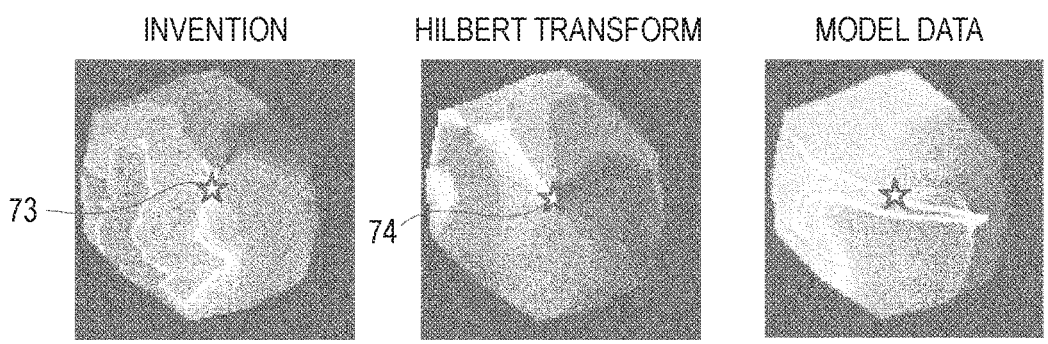
SAMPLE 3
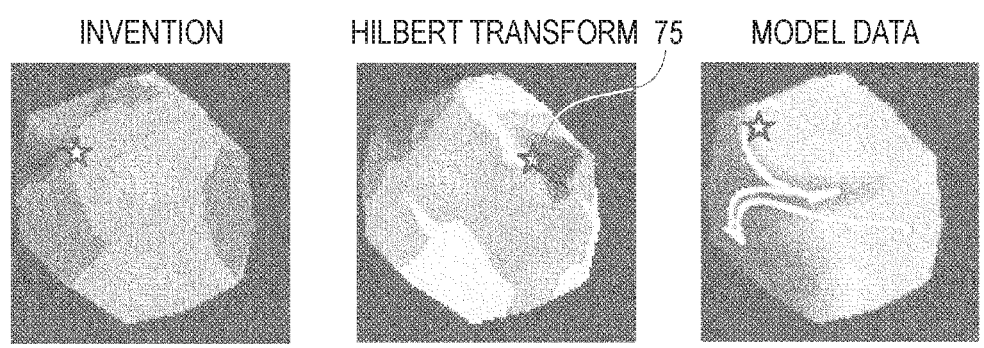

FIG. 19
SAMPLE 4
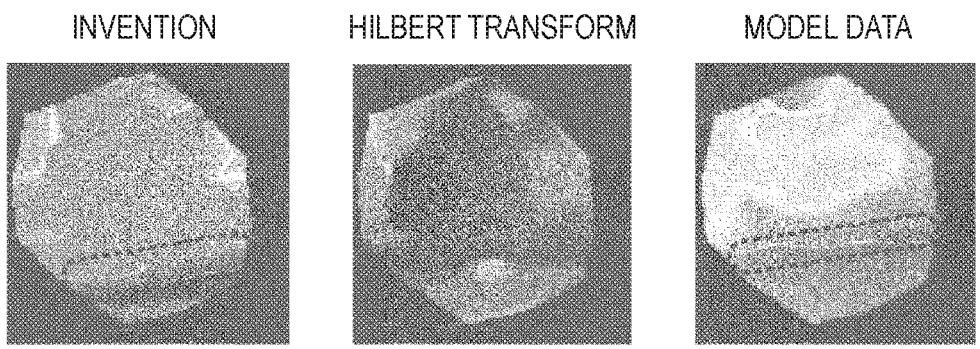
INVENTION　　　HILBERT TRANSFORM　　　MODEL DATA
SAMPLE 5　　　　　　　　　　INFLUENCE OF NOISES
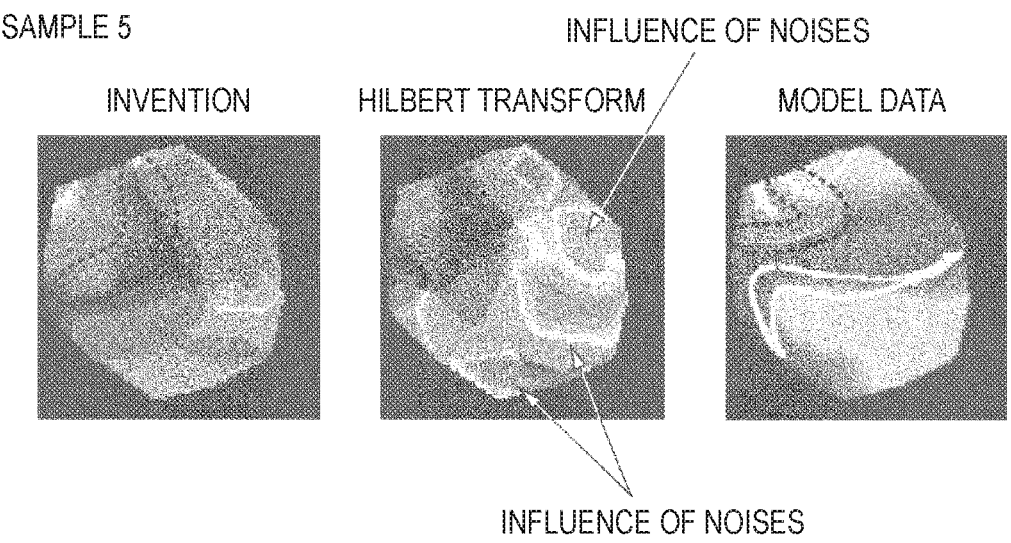
INVENTION　　　HILBERT TRANSFORM　　　MODEL DATA
INFLUENCE OF NOISES
SAMPLE 6
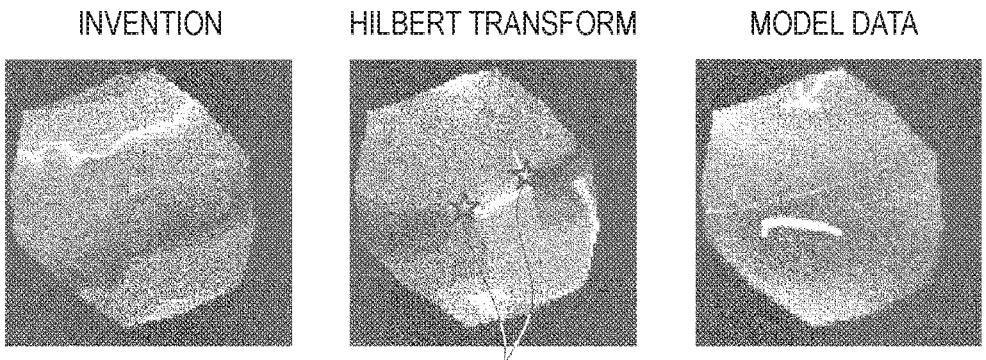
INVENTION　　　HILBERT TRANSFORM　　　MODEL DATA
76

MYOCARDIAL ANALYSIS APPARATUS AND MYOCARDIAL EXCITATION DETECTION APPARATUS

BACKGROUND

Technical Field

The present invention relates to a myocardial excitation complementation/visualization apparatus for visualizing the state of excitation in the myocardium, and also to a myocardial excitation detection apparatus for detecting excitation in the myocardium.

Background Art

Generally, atrial fibrillation means an arrhythmia in which the atrium of the heart has a convulsive seizure, and the heart cannot operate in the original and correct way. When the atrial fibrillation occurs, the blood stagnates in the atrium, and thrombus is prone to be formed, thereby increasing the possibility of occurrence of brain infarction or the like.

Conventionally, it is known that, when an arrhythmia such as atrial fibrillation occurs, a treatment is performed by selectively applying ablation to an abnormal portion which causes the arrhythmia, by using a cardiac catheter. In the treatment, it is important to correctly identify the location where ablation is to be performed.

For example, JP-T-2013-523344 and US 2014/0088395 A1 propose a technique in which a computation process is performed on an intracardiac electrocardiogram that is measured from electrodes of a cardiac catheter, thereby preparing visualized data indicating the state of excitation in the myocardium, and the location where ablation is to be performed is identified from the visualized data.

In the prior art, in a computation process of visualizing the state of excitation in the myocardium, the Hilbert transform is performed on an intracardiac electrocardiogram. Thereafter, a phase portrait is prepared based on the intracardiac electrocardiogram before the Hilbert transform, and the intracardiac electrocardiogram after the Hilbert transform, and visualized data (phase map) are generated from the phase portrait.

In the Hilbert transform, however, a fast Fourier transform (FFT) and an inverse fast Fourier transform (IFFT) are performed in one computation, and therefore throughput of the computation process is huge. In order to visualize a change of the state of excitation in the myocardium, moreover, the computation process of the Hilbert transform must be repeatedly performed on each of a plurality of intracardiac electrocardiograms which are recorded by a plurality of electrodes attached to the cardiac catheter. Because of the huge computation amount, under present circumstances, the application of the prior art using the Hilbert transform is limited to a use in an off-line mode.

In the prior art, as described above, it is difficult to continuously prepare visualized data with respect to an intracardiac electrocardiogram which is recorded by a cardiac catheter, and display the data in real time.

Therefore, it is an object of the invention to provide a myocardial excitation complementation/visualization apparatus which can complement, visualize, and display the state of excitation in the myocardium in real time, and a myocardial excitation detection apparatus which can enhance the accuracy of detecting the position of excitation in the myocardium.

SUMMARY OF THE INVENTION

In order to attain the aforementioned object, a myocardial excitation complementation/visualization apparatus includes an acquiring section that acquires intracardiac electrocardiograms of a subject, the intracardiac electrocardiograms being recorded by a recording unit having a plurality of electrodes, a processing section that performs a computation for completing and visualizing a state of excitation in a myocardium of the subject based on the intracardiac electrocardiograms, and a displaying section that displays the state of excitation in the myocardium of the subject based on an output of the processing section. In the myocardial excitation complementation/visualization apparatus, the processing section includes a first generating section which, with respect to each of the plurality of intracardiac electrocardiograms that are recorded by the plurality of electrodes of the recording unit, generates a pseudo action potential waveform, a correcting section which performs a correction for equalizing amplitudes of unit waveforms contained in the action potential waveforms, a second generating section which, with respect to each of the action potential waveforms corrected by the correcting section, generates a shifted waveform that is different in time phase from the action potential waveform, and a third generating section which prepares a phase portrait based on each of the action potential waveforms corrected by the correcting section, and the shifted waveform corresponding to the action potential waveform, and which generates visualized data indicating the state of excitation in the myocardium of the subject, based on the phase portraits. The displaying section displays a change of the state of excitation in the myocardium of the subject based on the visualized data.

According to the configuration, in place of the Hilbert transform, pseudo action potential waveforms and corresponding shifted waveforms are prepared from intracardiac electrocardiograms, phase portraits are generated from these waveforms, and visualized data are generated. According to the configuration, the computation amount for generating visualized data can be remarkably reduced. Before the preparation of the shifted waveforms, the correction of equalizing the amplitudes of the unit waveforms is performed on the pseudo action potential waveforms. Therefore, the positions of the centers of data in the phase portraits can be equalized with one another, and, even when the Hilbert transform is not used, the state of excitation in the myocardium can be reflected in the visualized data. According to the configuration, as described above, the computation amount for generating visualized data indicating the state of excitation in the myocardium is remarkably reduced as compared with the prior art. Therefore, visualized data can be continuously prepared with respect to intracardiac electrocardiograms recorded by the recording unit, and the state of excitation in the myocardium can be displayed in real time.

Moreover, the myocardial excitation interpolation/visualization apparatus of the invention includes an acquiring section that acquires intracardiac electrocardiograms of a subject, the intracardiac electrocardiograms being recorded by a recording unit having a plurality of electrodes, a processing section that performs a computation for completing and visualizing a state of excitation in a myocardium of the subject based on the intracardiac electrocardiograms, a displaying section that displays state of excitation in a myocardium of the subject based on an output of the processing section, and a storage section that stores a plurality of action potential unit waveforms that are previously generated by computer simulation. In the myocardial excitation interpolation/visualization apparatus, the processing section includes a first generating section which, with respect to each of the plurality of intracardiac electrocardiograms that are recorded by the plurality of electrodes of the recording unit, generates a pseudo action potential waveform by using the action potential unit waveforms, a second generating section which, with respect to each of the action potential waveforms, generates a shifted waveform that is different in time phase from the action potential waveform, and a third generating section which prepares a phase portrait based on each of the action potential waveforms and the shifted waveform corresponding to the action potential waveform, and which generates visualized data indicating the state of excitation in the myocardium of the subject, based on the phase portraits. The displaying section displays a change of the state of excitation in the myocardium of the subject based on the visualized data.

According to the configuration, in place of the Hilbert transform, pseudo action potential waveforms and corresponding shifted waveforms are generated from intracardiac electrocardiograms, phase portraits are prepared from these waveforms, and visualized data are generated. According to the configuration, the computation amount for generating visualized data can be remarkably reduced. Moreover, pseudo action potential waveforms are generated by using the action potential unit waveforms that are generated by computer simulation. Therefore, it is possible to suppress influences due to far field potentials (potentials due to portions which are remote from the electrodes) and noises that may be contained in the intracardiac electrocardiogram waveforms, and the state of excitation in the myocardium can be accurately reflected in the visualized data. According to the configuration, therefore, visualized data can be continuously prepared from intracardiac electrocardiograms recorded by the recording unit, and the state of excitation in the myocardium can be displayed in real time.

Moreover, the myocardial excitation detection apparatus of the present invention includes an acquiring section that acquires intracardiac electrocardiograms of a subject, the intracardiac electrocardiograms being recorded by a recording unit having a plurality of electrodes, and a processing section that performs a computation for completing and visualizing a state of excitation in a myocardium of the subject based on the intracardiac electrocardiograms. In the myocardial excitation detection apparatus includes a first generating section which, with respect to each of the plurality of intracardiac electrocardiograms that are recorded by the plurality of electrodes of the recording unit, generates a pseudo action potential waveform, a second generating section which, with respect to each of the action potential waveforms, generates a shifted waveform that is different in time phase from the action potential waveform, a third generating section which prepares a phase portrait based on each of the action potential waveforms and the shifted waveform corresponding to the action potential waveform, and which generates visualized data indicating the state of excitation in the myocardium of the subject, based on the phase portraits, and a detecting section which extracts a first grid set that is configured by a predetermined number of grids, from the visualized data, and which detects a center of the first grid set as a phase singularity in a case where a total of color differences between adjacent grids in the first grid set is equal to or larger than a predetermined value, and all of predetermined colors are contained in a second grid set that is centered on the first grid set, and that is configured by grids a number of which is larger than a number of the grids in the first grid set.

According to the configuration, in place of the Hilbert transform, pseudo action potential waveforms and corresponding shifted waveforms are prepared from intracardiac electrocardiograms, phase portraits are generated from these waveforms, and visualized data are generated. Therefore, the computation amount for generating visualized data can be remarkably reduced as compared with the prior art, and visualized data can be continuously prepared with respect to intracardiac electrocardiograms recorded by the recording unit. According to the configuration, the accuracy of detecting a phase singularity indicating the center of the rotor of chronic atrial fibrillation can be enhanced.

According to the myocardial excitation complementation/visualization apparatus of the invention, the state of excitation in the myocardium can be visualized and displayed in real time, and, according to the myocardial excitation detection apparatus, the accuracy of detecting the position of excitation in the myocardium can be enhanced.

BRIEF DESCRIPTION OF DRAWINGS

FIG. 4A is a view illustrating steps of generating a pseudo action potential waveform, and FIG. 4B is a view illustrating steps of detecting beats.

FIG. 6A is a view illustrating steps of detecting the initial beat, and FIG. 6B is a view illustrating steps of detecting the second and subsequent beats.

FIG. 13A is a view showing colors used in the painting, FIG. 13B is a view in which portions of an action potential waveform are defined by colors for every sample, and FIG. 13C is a view illustrating angle information of samples.

FIG. 18 is a view illustrating comparison examples of visualized data.

FIG. 19 is a view illustrating comparison examples of visualized data.

DETAILED DESCRIPTION OF EMBODIMENTS

Hereinafter, an example of the embodiment will be described in detail with reference to the drawings.

Embodiment 1

Figure 1:
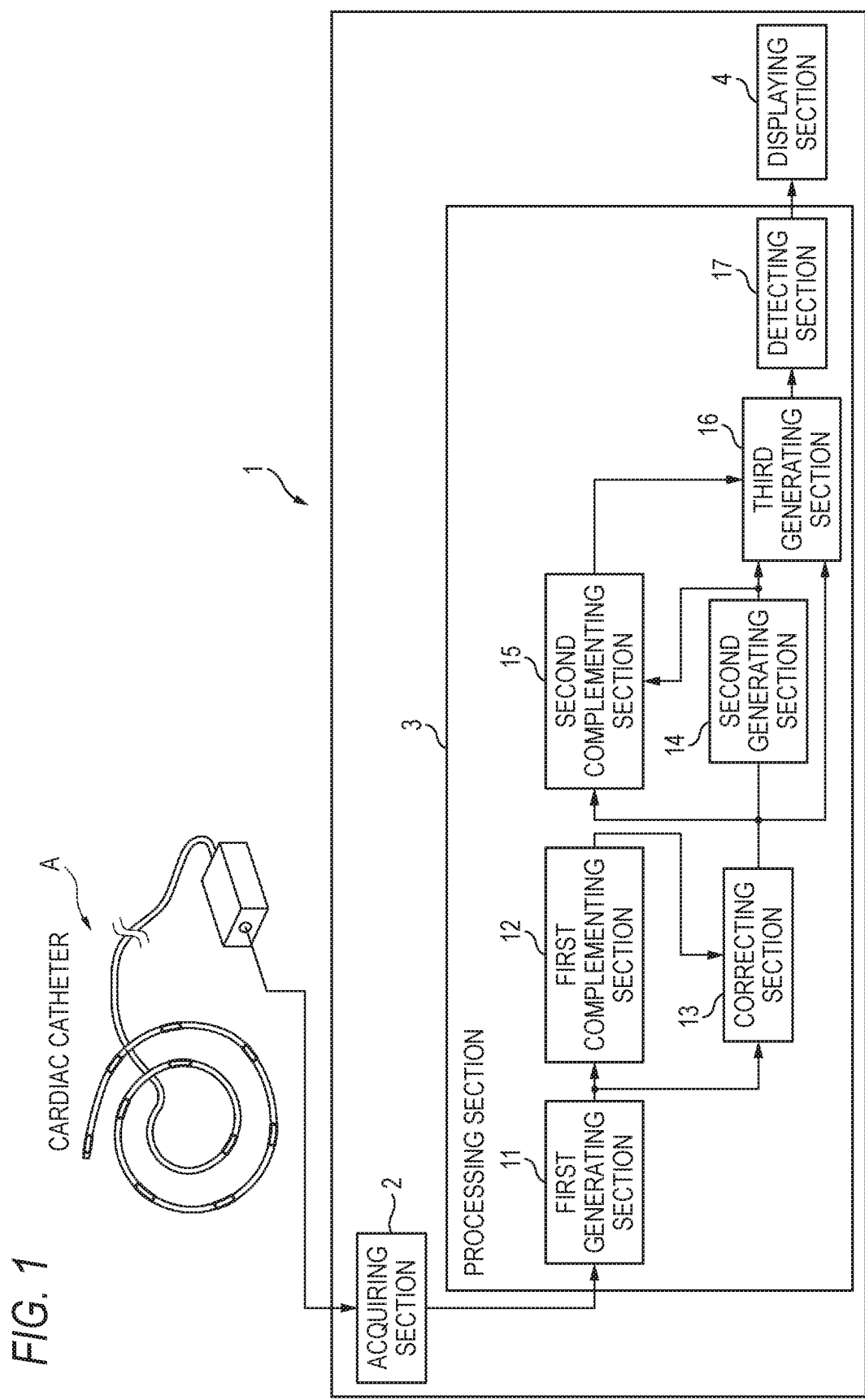
FIG. 1 is a diagram of a myocardial excitation complementation/visualization apparatus of Embodiment 1 of the invention.

As shown in FIG. 1, a myocardial excitation complementation/visualization apparatus 1 of Embodiment 1 includes an acquiring section 2, a processing section 3, and a displaying section 4. For example, the myocardial excitation complementation/visualization apparatus 1 is used as an apparatus for performing one function of a catheter inspection apparatus.

The acquiring section 2 acquires an intracardiac electrocardiogram of a subject which is recorded by a recording unit A (e.g., a cardiac catheter) having a plurality of electrodes.

The processing section 3 performs a computation for visualizing the state of myocardial excitation of the subject, on the intracardiac electrocardiogram which is acquired by the acquiring section 2. The processing section 3 includes a first generating section 11, a first complementing section 12, a correcting section 13, a second generating section 14, a second complementing section 15, a third generating section 16, and a detecting section 17.

The first generating section 11 generates pseudo action potential waveforms with respect to a plurality of intracardiac electrocardiograms which are acquired by the acquiring section 2, respectively.

The first complementing section 12 defines a virtual electrode at a position which is in the myocardium of the atrium, and in which the electrodes of the inserted cardiac catheter A are not placed, i.e., at a position in which the distances with respect to surrounding electrodes among the placed electrodes are large. The first complementing section 12 interpolates a pseudo action potential waveform with respect to the virtual electrode, based on pseudo action potential waveforms which are generated with respect to electrodes surrounding the virtual electrode.

The correcting section 13 performs a correction in which noise components contained in the pseudo action potential waveforms output from the first generating section 11 and the first complementing section 12 are eliminated, and the amplitudes at respective beats are equalized. In the following description of Embodiment 1, a corrected action potential waveform is referred to simply as an action potential waveform.

With respect to each of the action potential waveforms output from the correcting section 13, the second generating section 14 generates a shifted waveform which is shifted in time phase by a predetermined time from the action potential waveform.

With respect to a position in which the electrodes of the cardiac catheter A and the virtual electrode are not placed, i.e., a position in which the distances between each electrode and surrounding electrodes are large, the second complementing section 15 interpolates an action potential waveform and a shifted waveform based on the action potential waveforms and shifted waveforms which are generated with respect to the surrounding electrodes.

The third generating section 16 prepares a phase portrait based on the action potential waveforms output from the correcting section 13, the shifted waveforms output from the second generating section 14, and the action potential waveforms and shifted waveforms output from the second complementing section 15. Moreover, the third generating section 16 calculates the phase based on the phase portrait, and generates visualized data indicating the state of excitation in the myocardium. The visualized data mean a map in which the excitation potential of the myocardium is visualized. Electrical excitation occurs in the membrane potential of the myocardium cells to cause the heart to contract. The excitation-contraction phenomenon is provoked by the action potential. The action potential is an excitation reaction of myocardial cells which is caused by depolarization generated by the flow of $Na^+$ into the cells, and repolarization generated by the flow in or out of $Ca^{2+}$ or $K^+$.

The detecting section 17 detects a phase singularity in the visualized data generated by the third generating section 16, i.e., the rotor of fibrillation on the atrial wall.

The displaying section 4 displays the state of excitation in the myocardium of the subject based on the visualized data output from the third generating section 16 of the processing section 3. The displaying section 4 is configured by, for example, a liquid crystal monitor screen of the touch panel type.

Next, the operation of the myocardial excitation complementation/visualization apparatus 1 will be described with reference to FIGS. 2 to 16.

Figure 2:
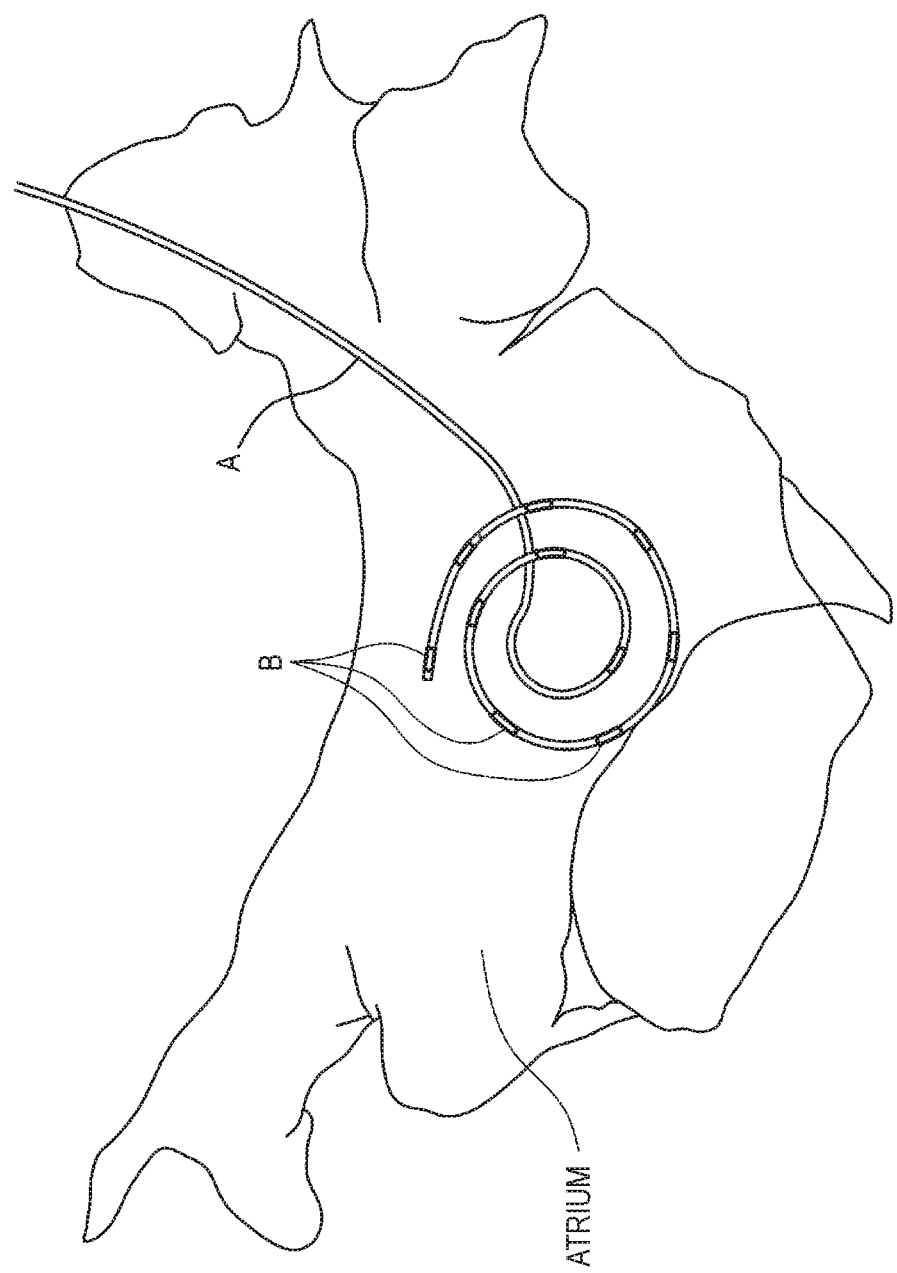
FIG. 2 is a diagram illustrating a catheter which is placed in the atrium.

As shown in FIG. 2, first, the cardiac catheter A having a plurality of electrodes B is inserted and placed in the atrium of the subject.

Figure 3A:
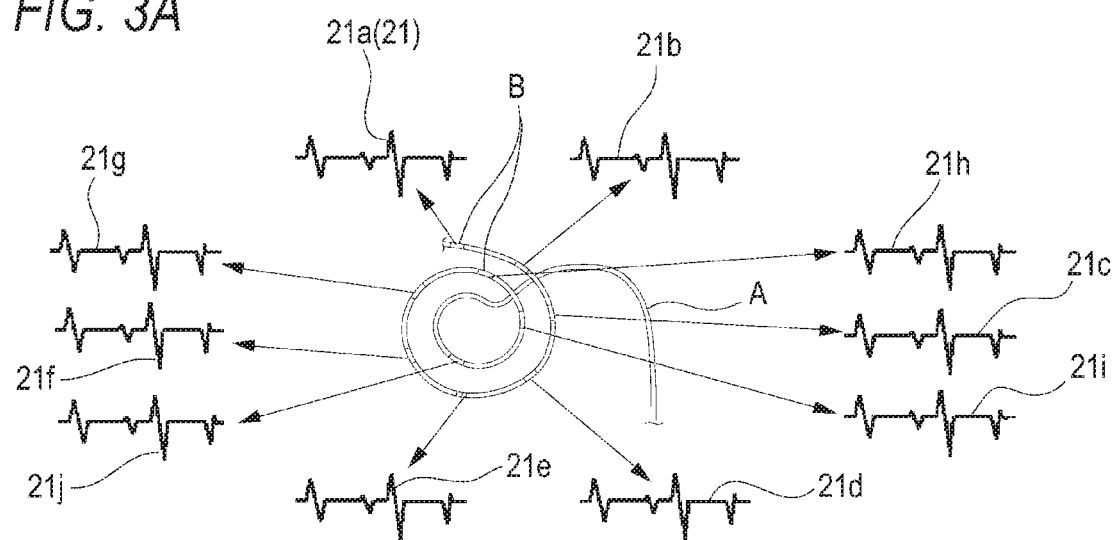
FIG. 3A is a diagram illustrating examples of intracardiac electrocardiogram waveforms which are acquired by electrodes.

As shown in FIG. 3A, a plurality (in the example, ten) of intracardiac electrocardiogram waveforms 21a to 21j (hereinafter, "intracardiac electrocardiogram waveforms 21" is used when generally referring to the intracardiac electrocardiogram waveforms) are recorded by the electrodes B of the cardiac catheter A. The recorded intracardiac electrocardiogram waveforms 21 are acquired by the acquiring section 2.

Figure 3B:
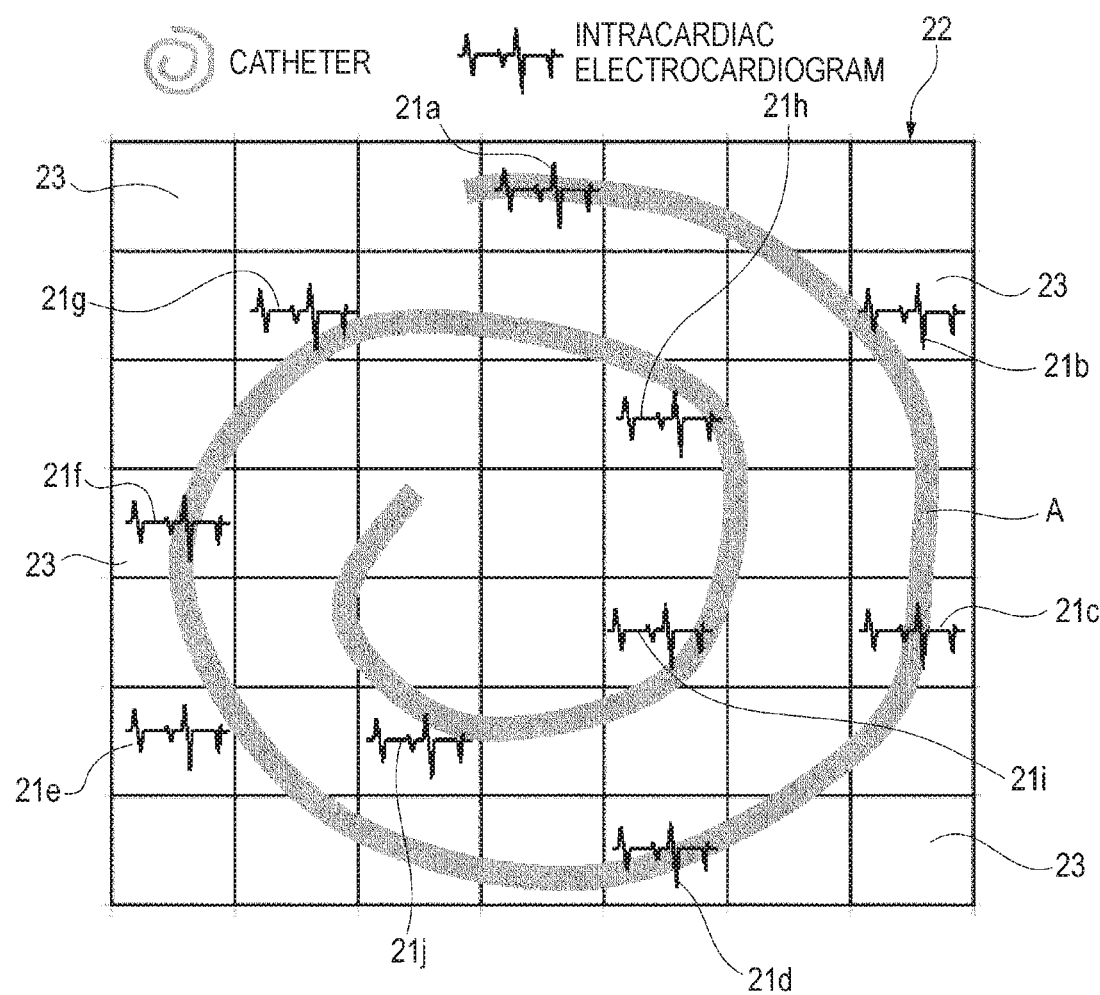
FIG. 3B is a diagram of a placement of the acquired intracardiac electrocardiograms on grids.

As shown in FIG. 3B, the first generating section 11 illustrates a predetermined region in the atrium in which the cardiac catheter A is placed, as a rectangular map 22 or the like, and partitions the map 22 into a plurality of grids 23. In the diagram of FIG. 3B, for the sake of convenience of description, 7×7=49 grids are shown, but actually the map is partitioned into several tens of thousands or more of grids. In accordance with the position of the cardiac catheter A placed in the atrium, the positions of the electrodes B are shown on the corresponding grids in the map, and the intracardiac electrocardiogram waveforms 21a to 21j are placed on the grids 23, respectively.

As shown in FIG. 4A, the first generating section 11 rectifies each of the intracardiac electrocardiogram waveforms 21 to prepare a rectified waveform 24. Moreover, the first generating section 11 performs moving average of the rectified waveform 24 to prepare a pseudo action potential waveform 25.

As shown in FIG. 4B, furthermore, the first generating section 11 detects candidates of beats (beat candidates) 28 indicating the diastoles of the myocardium in the pseudo action potential waveform 25, based on the pseudo action potential waveform 25 and the intracardiac electrocardiogram waveform 21. Specifically, the first generating section 11 first detects, in the pseudo action potential waveform 25, convex portions 26 in each of which a larger portion does not exist within time periods of 37 msec (described later with reference to FIGS. 5A and 5B) preceding and succeeding the each convex portion 26. Then, the first generating section 11 detects, in the intracardiac electrocardiogram waveform 21, beats 27 which are in phase with the respective convex portions 26, and which satisfy predetermined conditions (described later with reference to FIG. 5C). In the case where a convex portion 26 contains a beat 27 satisfying the predetermined conditions, the first generating section 11 detects the convex portion 26 as a beat candidate 28 indicating the diastole of the myocardium. In FIG. 4B, four beat candidates 28 are detected.

Figure 5B:
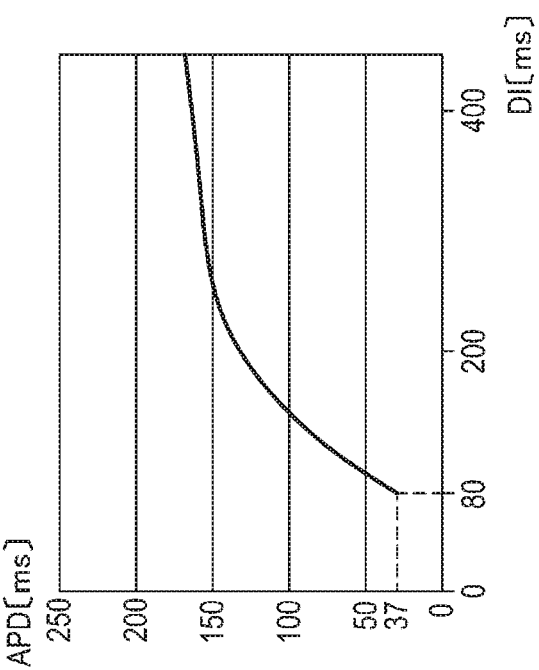
FIG. 5B is a graph illustrating relationships between a diastolic interval and an action potential duration.
Figure 5A:
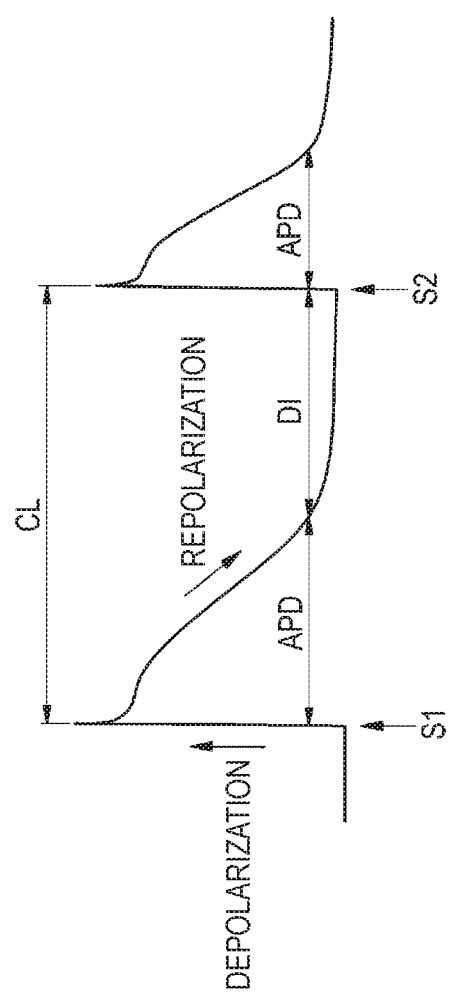
FIG. 5A is a view illustrating a diastolic interval and an action potential duration.
Figure 5C:
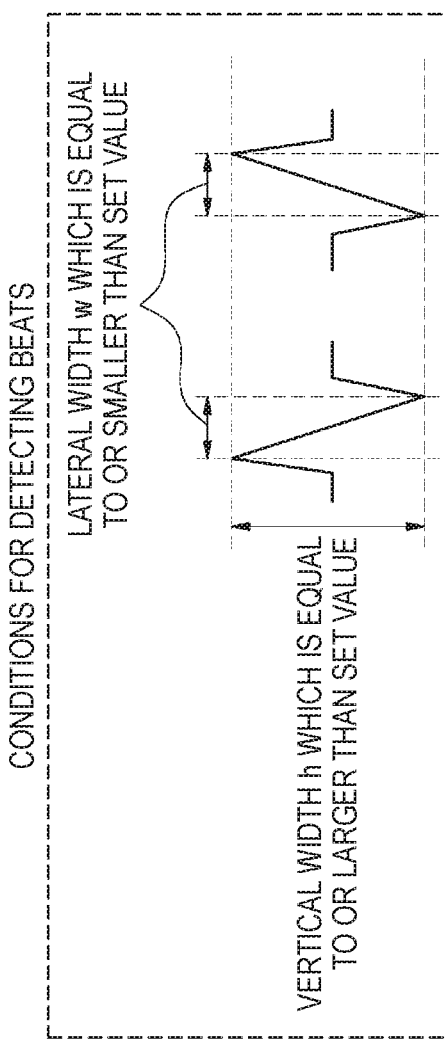
FIG. 5C is a view illustrating conditions for detecting beats.

FIG. 5A illustrates an ideal model of a unit waveform contained in the action potential waveform of the myocardium. In FIG. 5A, the term of action potential duration (APD) means a time period from the start of the depolarization phase of the action potential of the myocardium, to the end of the repolarization phase, and corresponds to the refractory period of the myocardium. The term of diastolic interval (DI) means a time period from the end of the APD to the start of the next APD, and corresponds to the stationary phase when the myocardium is excitable. The total time period of the APD and the DI is called the cycle length (CL). The relationships between the DI and APD in the ideal model of a unit waveform are previously obtained by computer simulation as shown in the graph of FIG. 5B. As shown in the graph, the above-described periods of 37 msec are determined with reference to the shortest APD. The above-described predetermined conditions of the beat 27 are set that, as shown in FIG. 5C, the lateral width w of the beat 27 is equal to or smaller than a preset value, and the vertical width h is equal to or larger than a preset value.

As shown in FIG. 6A, then, the first generating section 11 compares the heights of the peaks of all beat candidates (in the example, beat candidates 28a, 28b) which exist in the shortest CL starting from the initial beat candidate 28a, with one another. The first generating section 11 detects the beat candidate 28a having the highest peak as the first beat (an example of the unit waveform) 29A. From the graph of FIG. 5B, the shortest CL is 117 msec which is obtained by adding 37 msec that is the shortest APD, and 80 msec that is the shortest DI.

As shown in FIG. 6B, then, the first generating section 11 compares the heights of the peaks of all beat candidates (in the embodiment, beat candidates 28c, 28d) which exist in the shortest CL starting from the beat candidate 28c following the beat candidates 28a, 28b that are compared with each other in FIG. 6A, with one another. The first generating section 11 detects the beat candidate 28d having the highest peak as the second beat (an example of the unit waveform) 29B. Same or similarly, the first generating section 11 detects beats from pseudo action potential waveforms 25a to 25j which are prepared based on the intracardiac electrocardiogram waveforms 21a to 21j, respectively.

Figure 7:
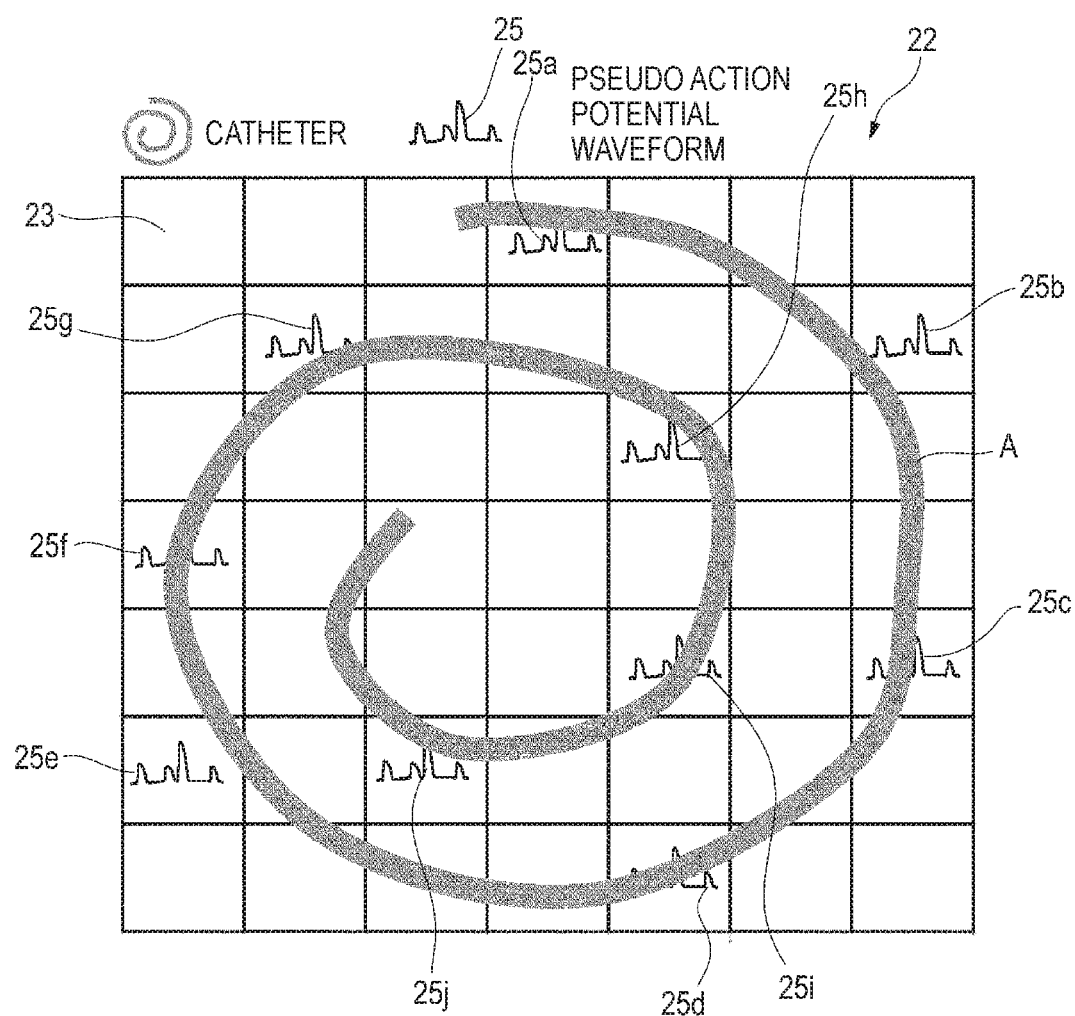
FIG. 7 is a diagram of a placement of pseudo action potential waveforms on grids.

The pseudo action potential waveforms 25a to 25j from which the beats 29A, 29B, etc. are detected are placed on the grids 23 (see FIG. 7).

Figure 8A:
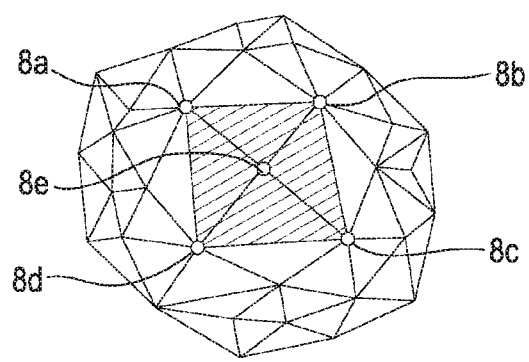
FIGS. 8A and 8B are views for calculating virtual electrodes.
Figure 8B:
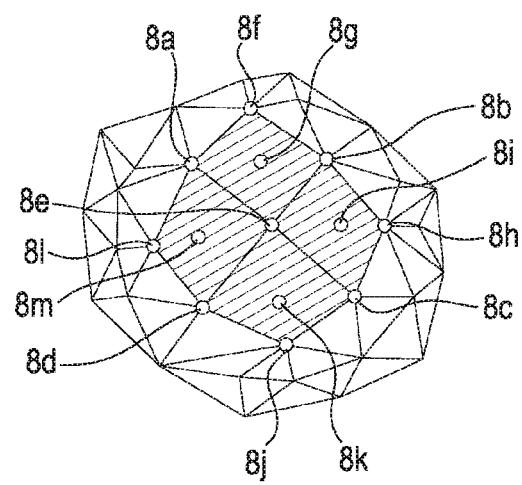
Figure 8C:
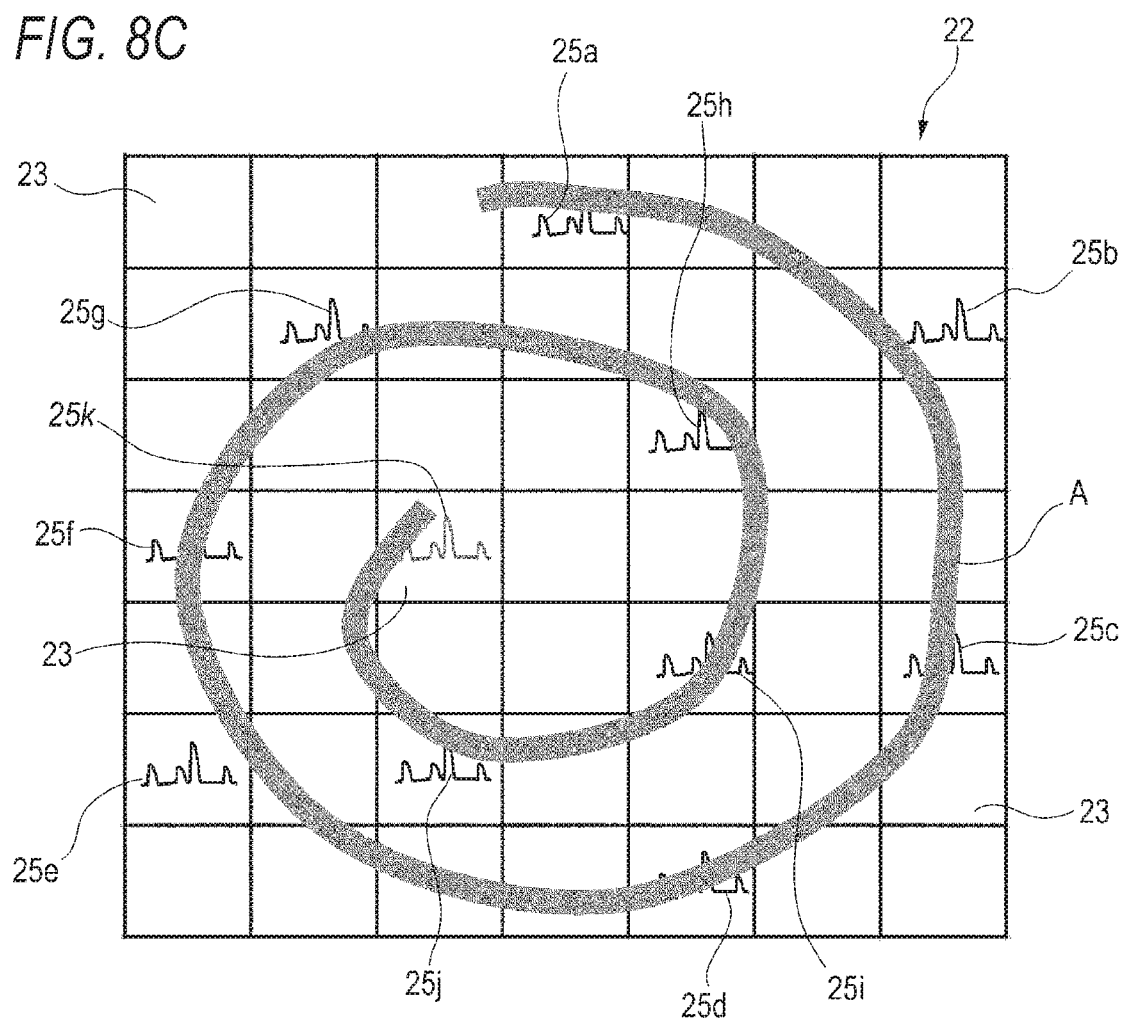
FIG. 8C is a diagram of a placement of an action potential waveform of a virtual electrode which is interpolated from surrounding electrodes.

Then, the first complementing section 12 defines virtual electrodes in locations where the pseudo action potential waveforms 25 are not placed, based on the positions of the pseudo action potential waveforms 25a to 25j which are placed in the map 22, and which are shown in FIG. 7. As shown in FIGS. 8A and 8B, each of the virtual electrodes is defined based on a plurality (in the example, four) of surrounding electrodes. In FIG. 8A, the position of a virtual electrode 8e is set based on position data of electrodes 8a to 8d. In FIG. 8B, the position of another virtual electrode 8g is set based on the virtual electrode 8e and electrodes 8a, 8b, 8f. The first complementing section 12 sets the positions of virtual electrodes 8i, 8k, 8m by using a same or similar technique.

The first complementing section 12 interpolates pseudo action potential waveforms 25 with respect to the defined virtual electrodes 8e, 8g, 8i, 8k, 8m, etc., based on pseudo action potential waveforms which are generated with respect to surrounding electrodes. For example, an interpolated pseudo action potential waveform 25k is placed on the grid 23 in the location where a virtual electrode is disposed (see FIG. 8C).

Figure 9A:
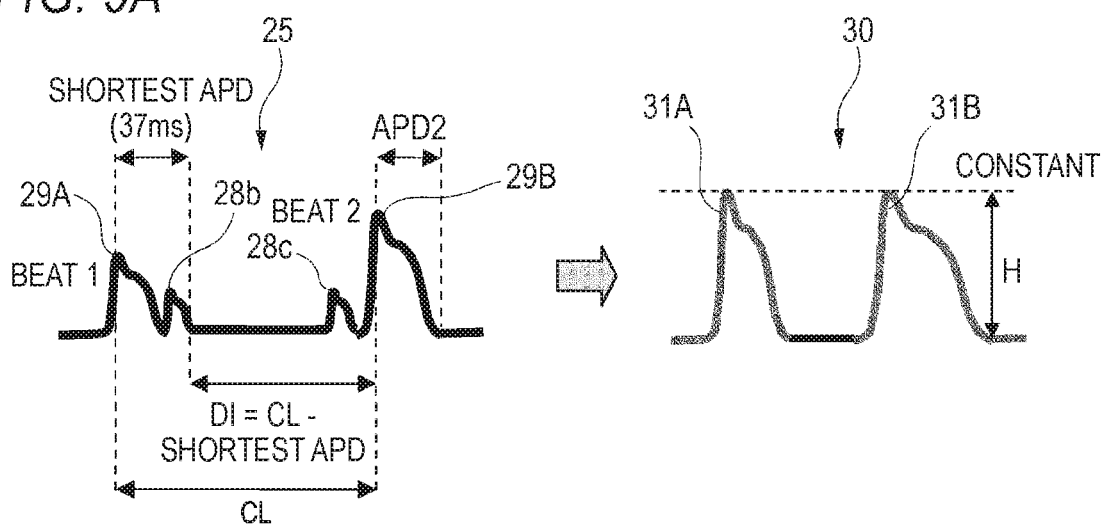
FIG. 9A is a view illustrating steps of correcting the height of a beat.
Figure 9B:
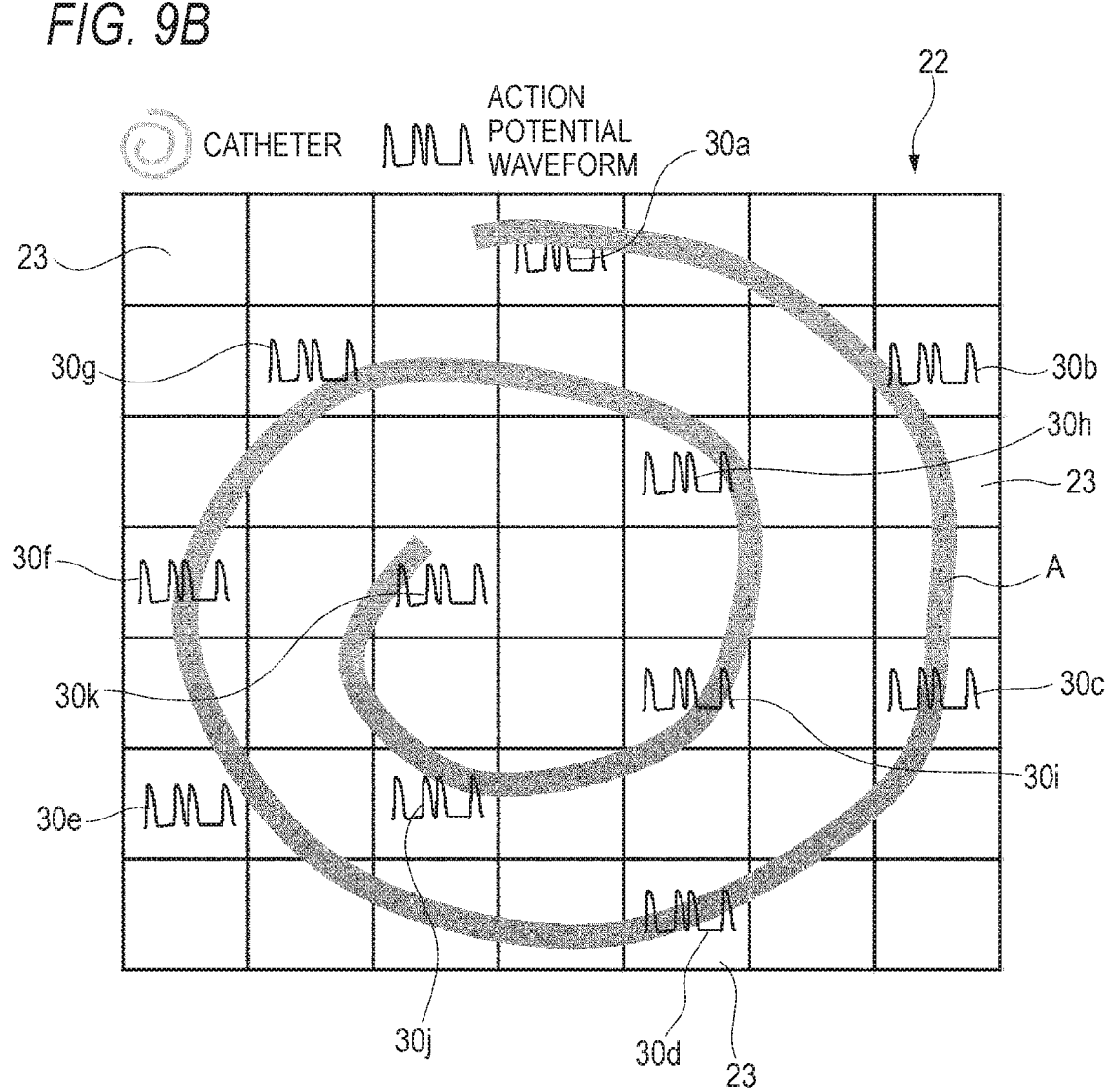
FIG. 9B is a diagram of a placement of action potential waveforms on grids.

As shown in FIG. 9A, then, the correcting section 13 prepares an action potential waveform 30 from the pseudo action potential waveform 25. Specifically, the correcting section 13 first applies the shortest APD (37 msec) to the first beat 29A of the pseudo action potential waveform 25. Then, the CL between the peak of the first beat 29A and that of the second beat 29B is obtained. The shortest APD is subtracted from the CL to obtain the value of the DI (DI=CL−shortest APD). Then, the value of the APD corresponding to the obtained value of the DI is obtained from the graph of FIG. 5B. The obtained value of the APD is the value of the APD2 of the second beat 29B. Similarly, the values of the APDs of the third and subsequent beats 29 are obtained.

Then, the correcting section 13 multiplies the beats 29A, 29B, etc. by a correction coefficient, thereby correcting the heights (amplitudes) of the beats to equalize the heights. The correction coefficient is obtained by dividing a constant by the height of the beat 29A, 29B, or the like (correction coefficient=constant/height of peak of beat 29). The correcting section 13 eliminates, by correction, beat candidates other than the beats 29A, 29B, etc. in the pseudo action potential waveform 25, such as the beat candidates 28b, 28c, etc. As a result, the action potential waveforms 30 having beats 31A, 31B, etc. in which their heights H are equal to one another are prepared with respect to the pseudo action potential waveforms 25, respectively. The corrected action potential waveforms 30a to 30k are placed on the grids 23 in the locations where the electrodes and the virtual electrodes are disposed (see FIG. 9B).

Figure 10A:
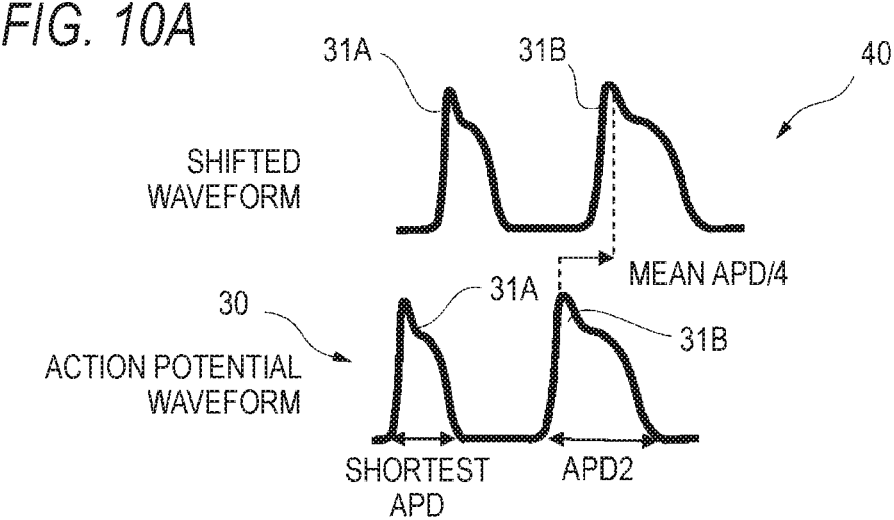
FIG. 10A is a view illustrating a shifted waveform in which the phase is shifted with respect to an action potential waveform.
Figure 10B:
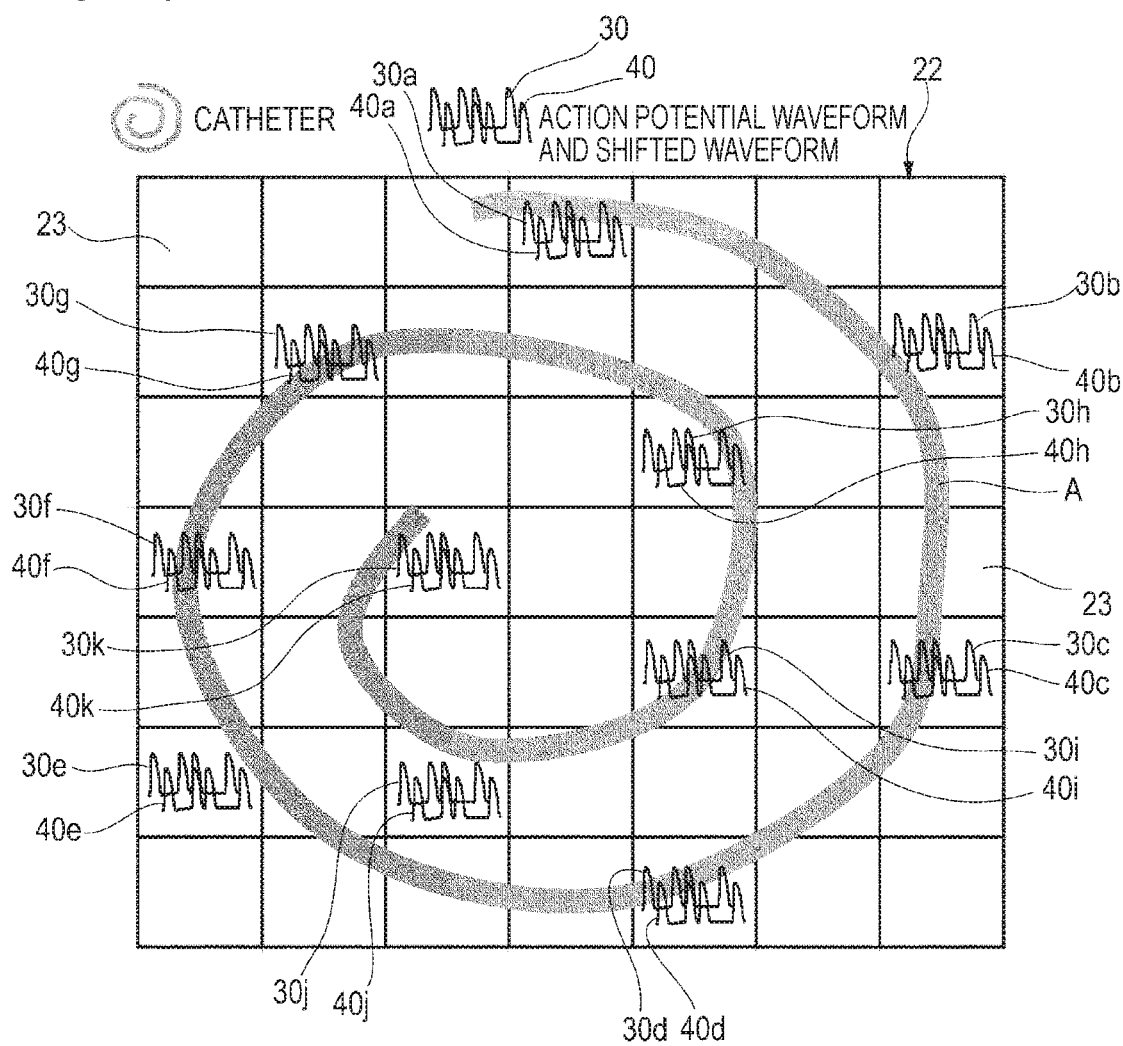
FIG. 10B is a diagram of a placement of action potential waveforms and shifted waveforms on grids.

Then, the second generating section 14 calculates a mean APD of the beats 31A, 31B, etc. in the action potential waveforms 30, and generates shifted waveforms 40 which, as shown in FIG. 10A, are shifted in time phase by ¼ of the mean APD from the action potential waveforms 30. The action potential waveforms 30a to 30k and the shifted waveforms 40a to 40k are placed on the grids 23 in the locations where the electrodes and the virtual electrodes are disposed (see FIG. 10B). The shift in time phase may be N+(¼) (N is 0 or a positive integer).

Figure 11A:
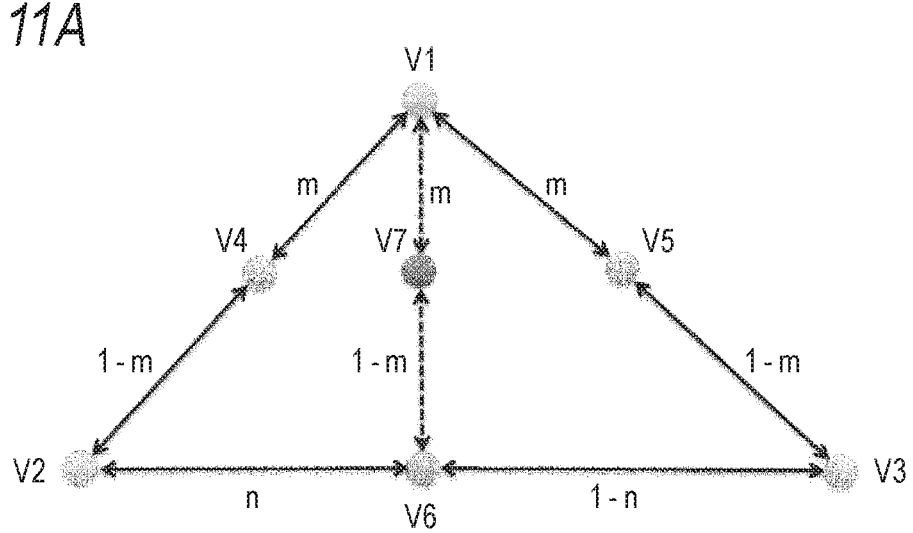
FIG. 11A is a view illustrating a calculation of interpolated waveforms on other grids in which the spatial interpolation technique is used.
Figure 11B:
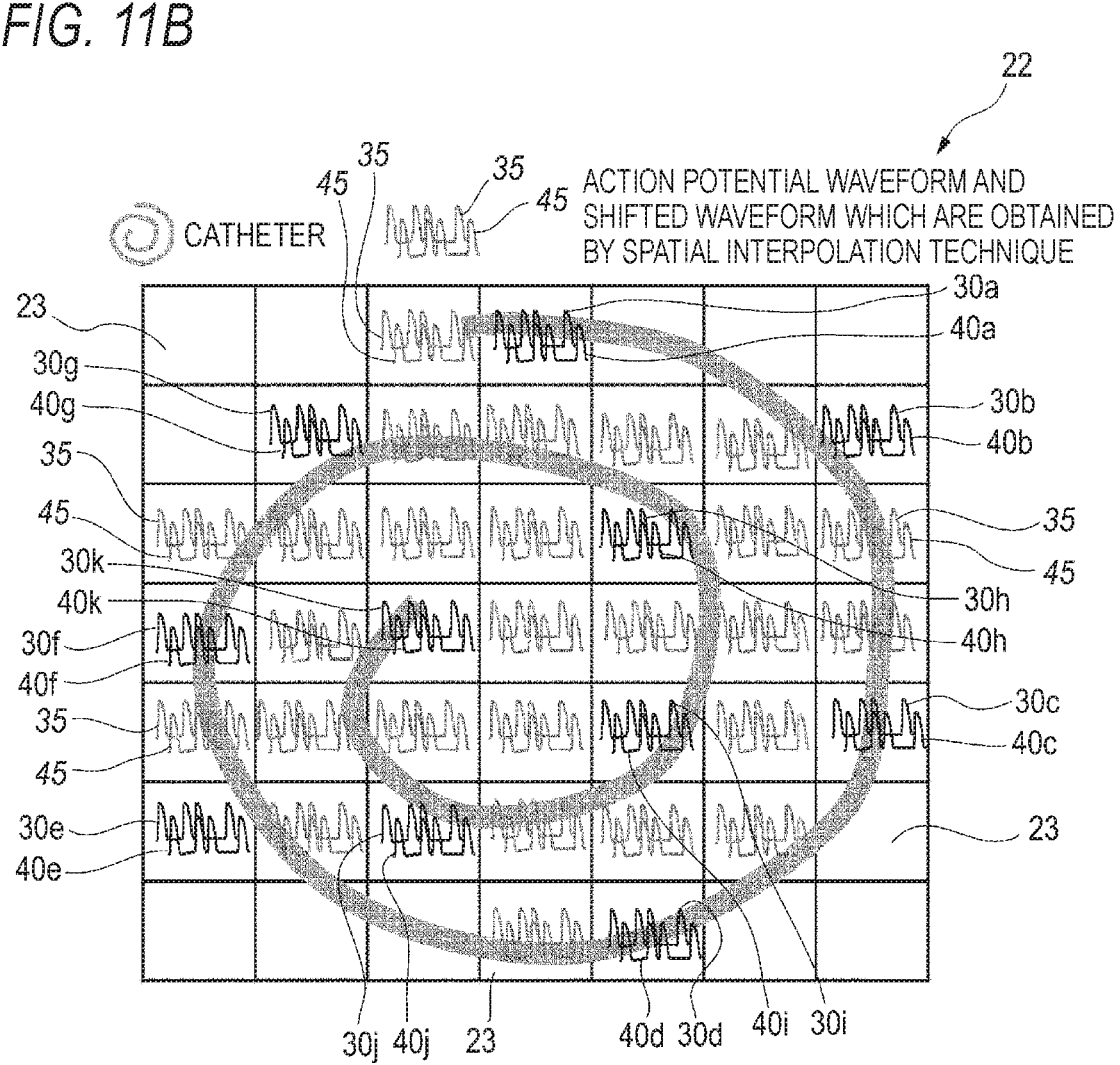
FIG. 11B is a diagram of a placement of interpolated action potential waveforms and shifted waveform on grids.

Then, the second complementing section 15 interpolates virtual action potential waveforms 35 and virtual shifted waveform 45 to grids 23 (see FIG. 10B) in which the action potential waveforms 30 and the shifted waveforms 40 are not placed on the map 22. The second complementing section 15 calculates data of the action potential waveforms 35 and the shifted waveforms 45, from those of the surrounding action potential waveforms 30 and shifted waveforms 40 by using the spatial interpolation technique shown in FIG. 11A. In FIG. 11A, V1 to V3 indicate the data of the action potential waveforms 30 and shifted waveforms 40 in the grids 23 of the electrodes and the virtual electrodes, and V4 to V7 indicate data of the action potential waveforms 35 and the shifted waveforms 45. The arrows indicate the distances between close grids among grids in which the data V1 to V7 are placed or to be placed. As an example, the distances between the grids are indicated as 1. From the data of the action potential waveforms 30 and shifted waveforms 40 of two grids which are close to the grid where the action potential waveform 35 and the shifted waveform 45 are to be placed, the data of the action potential waveform 35 and the shifted waveform 45 are calculated according to a predetermined calculation expression, by using the spatial interpolation technique, the data of the two grids, and the distance between the two grids. For example, the action potential waveform 35 and shifted waveform 45 of V4 are calculated from the data of V1 and V2, and the distances m, 1−m between V1 and V4, and V2 and V4. V7 is calculated from V6 which is calculated as described above, and the data V1 of the grid in which the action potential waveforms 30 and the shifted waveforms 40 are placed. The action potential waveforms 35 and shifted waveforms 45 which are calculated as described above are placed on the grids 23 in which the interpolation is performed (see FIG. 11B).

Figure 12:
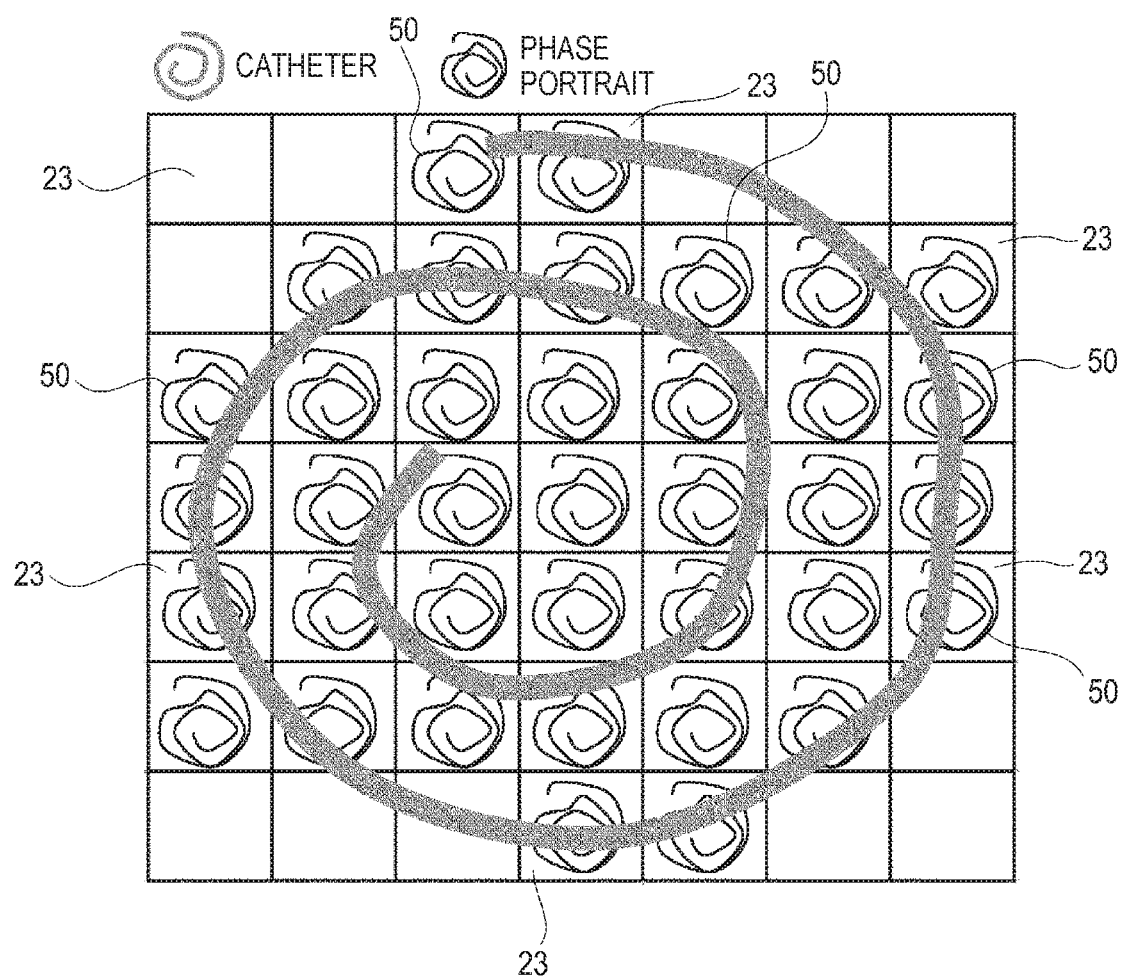
FIG. 12 is a diagram illustrating a phase portrait drawn in each grid.

In order to obtain the states of the action potentials in the grids 23 in which the action potential waveforms 30, 35 and the shifted waveforms 40, 45 are placed, then, the third generating section 16 prepares phase portraits 50 based on the respective action potential waveforms 30, 35 and shifted waveforms 40, 45 as shown in FIG. 12. A phase portrait can be prepared by rewriting the potentials of action potential waveforms and shifted waveforms to two-dimensional ones.

Figure 13A:
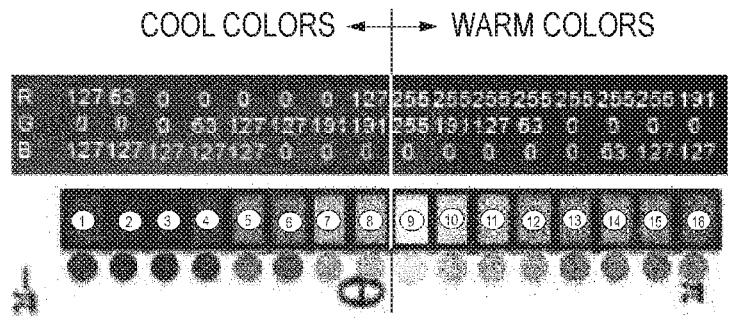
FIGS. 13A to 13C are views illustrating colors which are painted in grids.
Figure 13B:
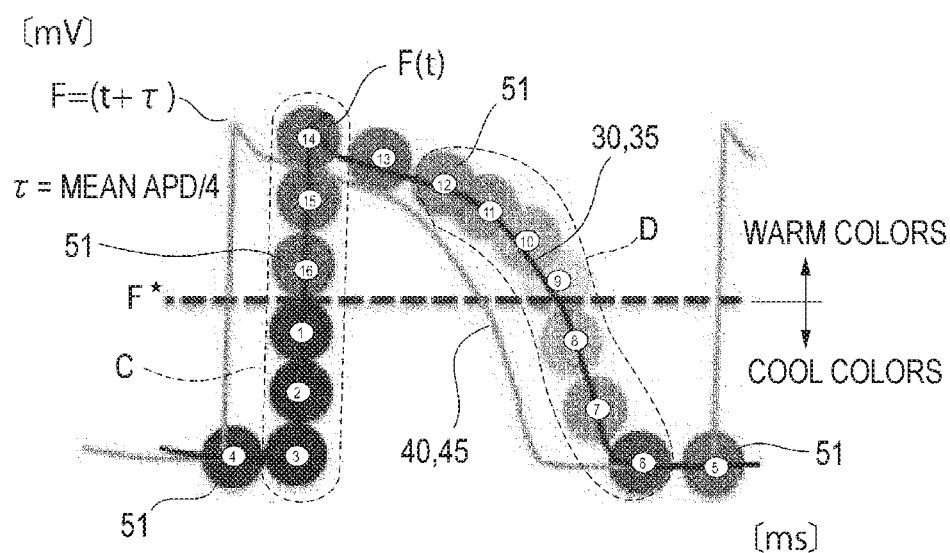
Figure 13C:
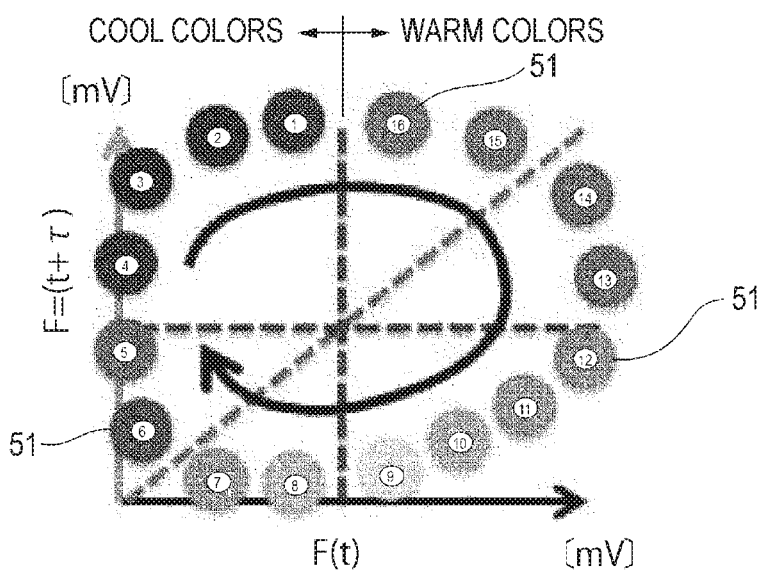

In order to express the states of the action potentials in colors, the third generating section 16 paints the grids 23 with colors. The colors of the grids 23 are determined for respective samples of the prepared phase portraits. The third generating section 16 draws the grids 23 by using a plurality of colors (in the example, 16 colors) shown in FIG. 13A. For example, the third generating section 16 defines colors so that, in unit waveforms of the action potential waveforms 30, 35, action potential portions are drawn in warm colors, and the resting membrane portions are drawn in cool colors (see FIG. 13B). The colors are defined so that, in the region C where the temporal variation in the action potential is fast, the color change between adjacent samples 51 is small, and, in the region D where the temporal variation is slow, the color change is large. As shown in FIG. 13C, the third generating section 16 obtains angle information of each of the samples 51 from the center portion of a phase portrait which is displayed while being replaced with a two-dimensional form, and expresses the state of the action potential by one of 16 colors.

Figure 14A:
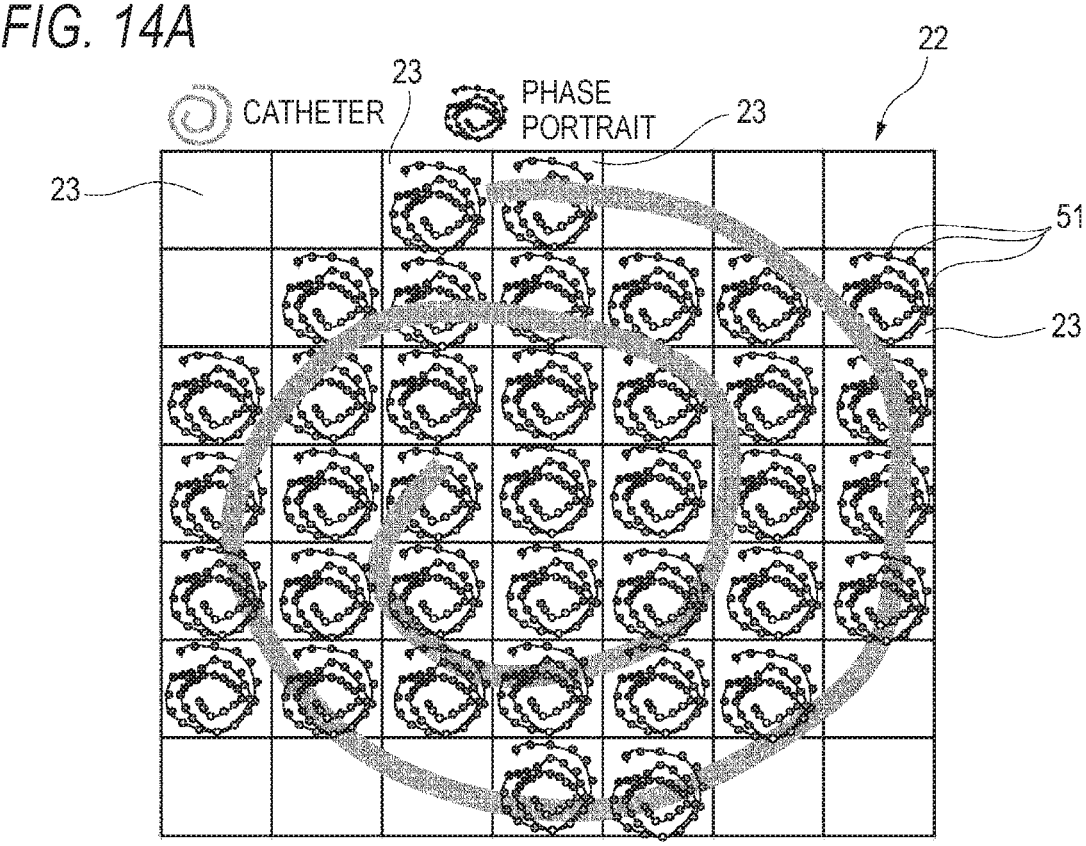
FIG. 14A is a diagram in which each sample is colored in each grid.
Figure 14B:
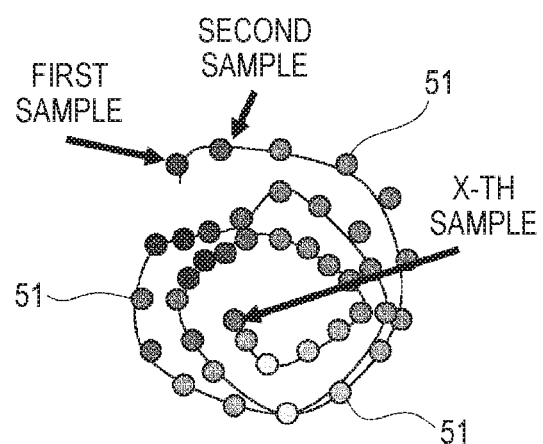
FIG. 14B is a view in which first to X-th samples in one grid are colored.
Figure 14C:
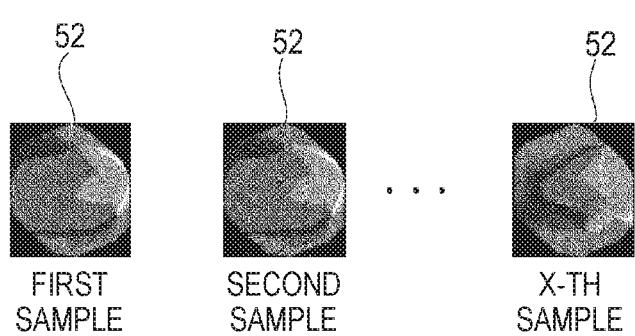
FIG. 14C is a view showing visualized data of the first to X-th samples.

As shown in FIGS. 14A and 14B, the third generating section 16 continuously paints the grids 23 with colors which are determined for respective samples in the grids 23. When colors for the first to X-th samples are continuously painted in each of the grids 23, continuous visualized data 52 such as shown in FIG. 14C are generated.

Figure 15:
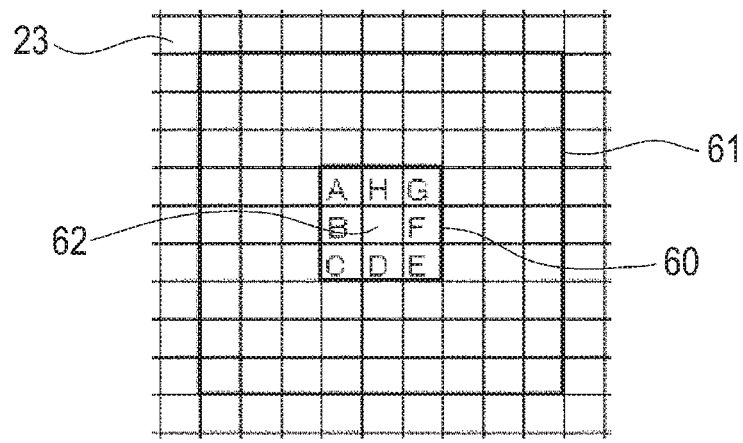
FIG. 15 is a view illustrating a method of detecting a phase singularity.

As shown in FIG. 15, then, the detecting section 17 extracts a first grid set 60 which is configured by a predetermined number (in the example, 3×3) of grids 23, from the map 22. The detecting section 17 further extracts a second grid set 61 that is centered on the first grid set 60, and that is configured by grids 23 the number (in the example, 9×9) of which is larger than that in the first grid set 60. The detecting section 17 calculates whether the total of color differences between adjacent grids (from grid A to grid H) in the first grid set 60 is equal to or larger than a predetermined value or not. Specifically, (color difference between A and B)+(color difference between B and C)+ . . . +(color difference between H and A) is calculated. The detecting section 17 further calculates whether all of the 16 colors are contained in the second grid set 61 or not. When both the conditions are satisfied, the detecting section 17 detects the center of the first grid set 60 as a phase singularity 62.

Figure 16:
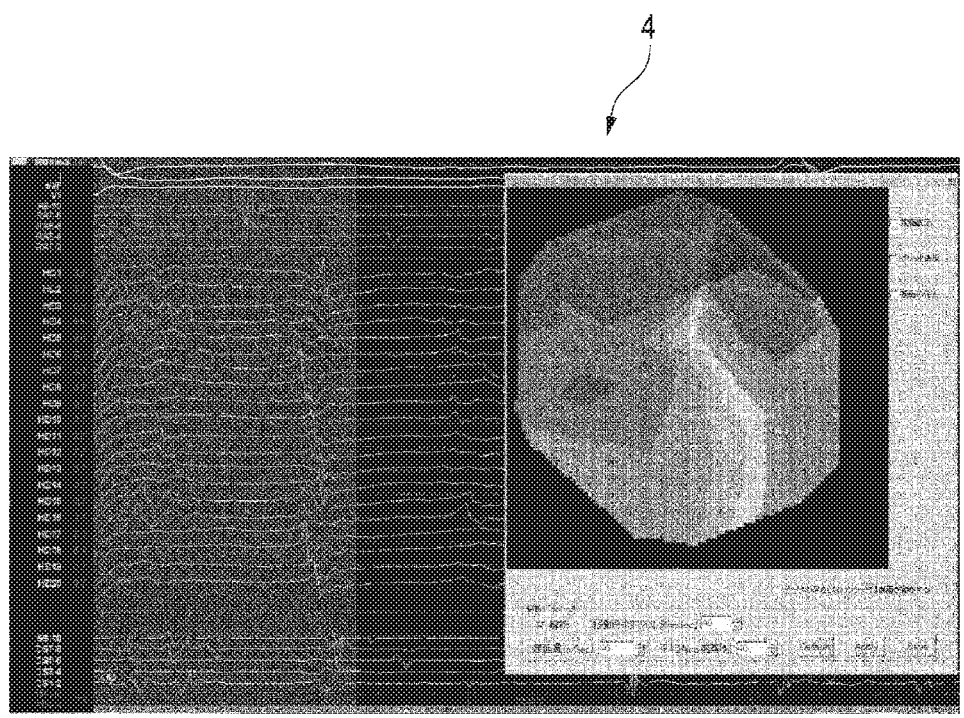
FIG. 16 is a view illustrating an example of visualized data which are displayed on a monitor screen.

On the screen of the displaying section 4, the visualized data are continuously displayed in a time sequential manner to be shown as a moving image, whereby the manner of change in the state of excitation in the myocardium of the subject is displayed in real time as shown in FIG. 16.

In the case where waveforms having beat information which is sufficient for analysis are not obtained from one of the electrodes B of the cardiac catheter A, the grid 23 related to the electrode B may be omitted from the drawing of the visualized data in order to maintain the accuracy of the visualized data. In this case, it may be determined whether beat information is sufficient or not, based on the cycle length value.

Figure 17A:
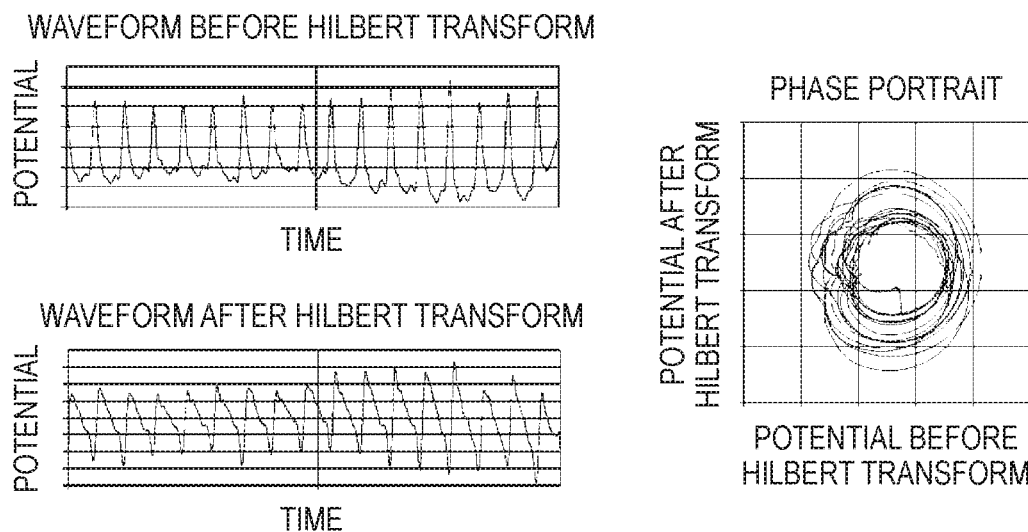
FIG. 17A is a view illustrating a prior art method in which a phase portrait is drawn by using the Hilbert transform.

As a calculation process for visualizing the state of excitation in the myocardium, there is the Hilbert transform. As shown in FIG. 17A, conventionally, a phase portrait is prepared based on an intracardiac electrocardiogram (a waveform before the Hilbert transform) recorded from the subject, and a waveform after the Hilbert transform, and visualized data are prepared from the phase portrait. In the Hilbert transform, however, an FFT and an IFFT are performed, and therefore the throughput of the computation process is huge. Therefore, the computation process takes a long time, and it is difficult to display the state of excitation in the myocardium in real time. In the Hilbert transform, an FFT and an IFFT are performed, and therefore the number of data to be analyzed is limited to a power of 2. Therefore, the degree of freedom of designation of the data analysis range is low, and there is a case where the analysis range cannot be adequately designated. In the Hilbert transform, moreover, a portion where myocardial excitation calms in a waveform after the Hilbert transform cannot be expressed (see the left lower figure in FIG. 17A). Namely, the rear surface of the waveform cannot be adequately indicated, and is different from an actual cardiac electrophysiological phenomenon. In the case where data which are visualized based on the Hilbert transform are reproduced as a moving image, therefore, correct expression is not performed.

Figure 17B:
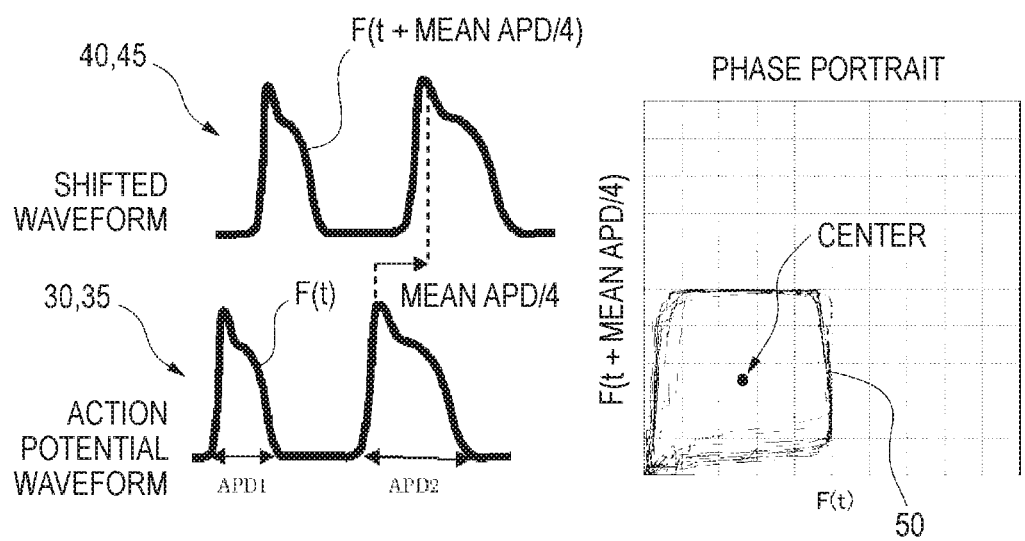
FIG. 17B is a view illustrating a method in the invention in which a phase portrait is drawn by using shifted waveforms and action potential waveforms.

According to the myocardial excitation complementation/visualization apparatus 1 of the embodiment, by contrast, the phase portrait 50 is prepared based on the action potential waveforms 30, 35 and the shifted waveforms 40, 45 as described above (see FIG. 17B). The action potential waveforms 30, 35 and the shifted waveforms 40, 45 can be generated by performing a process in which the computation amount is small, such as the height correction or the phase portrait shift, on the intracardiac electrocardiogram waveforms 21. Unlike the Hilbert transform, therefore, it is not necessary to perform an FFT and an IFFT, and the amount of the computation for generating the visualized data 52 can be remarkably suppressed.

Since the visualized data are prepared based on the action potential waveforms 30, 35 and the shifted waveforms 40, 45 as described above, moreover, an FFT and an IFFT are not required to be performed unlike the Hilbert transform. Therefore, the number of data to be analyzed is not limited, the degree of freedom of designation of the data analysis range is high, and the analysis range can be adequately designated.

In each of the action potential waveforms 30, 35 and the shifted waveforms 40, 45, a portion where the excitation rests is indicated in the rear surface of the waveform, and the phase portrait 50 is prepared based on the both waveforms (see FIG. 17B), and visualized data are prepared from the phase portrait. In the case where the visualized data are reproduced as a moving image, therefore, the process in which excitation calms is correctly expressed.

Before the shifted waveforms 40, 45 are generated based on the action potential waveforms 30, 35, a correction of equalizing the amplitudes of the beats 29A, 29B is performed on the pseudo action potential waveforms 25. Therefore, the positions of the centers of the samples 51 in the phase portrait 50 can be made equalized to one another, and, even when the Hilbert transform is not used, the state of excitation in the myocardium can be reflected in the visualized data.

In the case where the unit waveforms (the beats 29A, 29B) contained in the pseudo action potential waveforms 25 are to be extracted, moreover, the shortest CL in the ideal model of a unit waveform is used, and therefore the unit waveforms can be correctly extracted.

Moreover, the DI and APD of the action potential waveforms 30 are set based on the relationship of the DI and APD in the ideal model of a unit waveform. Therefore, it is possible to eliminate influences due to far field potentials (potentials due to excitations of portions which are remote from the electrodes) and noises which may be contained in the intracardiac electrocardiogram waveforms 21.

With respect to the pseudo action potential waveform 25k of a virtual electrode, the correction of the height of a beat, and the process of shifting the time phase are performed similarly with the pseudo action potential waveform 25 of a usual electrode. By contrast, with respect to a position in which the electrodes and the virtual electrode are not placed, the virtual action potential waveforms 35 and the virtual shifted waveform 45 are complemented by the spatial interpolation technique. As compared with the computation amount of the process that is performed at each of positions of virtual electrodes in which the number of interpolations is small, the computation amount of the process that is performed at each of positions where the electrode and the virtual electrode are not placed can be reduced, whereby the computation amounts of the two processes and the accuracy of the complementation data are balanced, and, even when the number of positions where both the electrodes and the virtual electrode are not placed is increased, the total computation amount can be suppressed.

In the region C where, in the action potential waveforms 30, 35, the phase change with respect to the elapse of time is large, the color change between the samples 51 is made small. Even when visualized data are displayed by using the spatial interpolation technique in a portion where the distance between electrodes is large, therefore, the isochrone can be smoothly drawn.

In the action potential waveforms 30, 35, a portion where the action potential exceeds the center of the phase portrait is defined with a warm color, and that where the action potential is lower than the center is defined with a cool color. Therefore, an observer who watches the monitor screen 4 can easily observe a change of the state of excitation in the myocardium.

Not only the first grid set 60, but also the second grid set 61 is used. Therefore, the accuracy of detecting the phase singularity 62 indicating the rotor of atrial fibrillation can be enhanced.

In this way, while reflecting the state of excitation in the myocardium to visualized data, the computation amount for generating visualized data can be remarkably reduced as compared to the prior art. Therefore, visualized data can be continuously prepared with respect to the intracardiac electrocardiograms 21 recorded from the cardiac catheter A, and the state of excitation in the myocardium can be displayed in real time. Since the Hilbert transform is not used, moreover, the analysis range can be adequately designated.

Next, FIGS. 18 and 19 show Comparison samples 1 to 6 of visualized data.

In Sample 1, when compared with the model data, the position (the star symbol 71) of the swivel center (rotor indicated by a phase singularity) of visualized data in the invention is correctly expressed at a position which is close to the position of the swivel center of the model data. In visualized data in the prior art technique in which the Hilbert transform is used, by contrast, the influence of noises appears, and the position of the swivel center is not correct.

In Sample 2, both the visualized data in the invention, and those obtained by the Hilbert transform correctly indicate the respective swivel centers (the star symbols 73, 74).

In Sample 3, the influence of noises strongly appears in the visualized data obtained by the Hilbert transform, and the swivel center (the star symbol 75) is not correctly indicated. By contrast, the visualized data in the invention indicate the swivel center at a position which is close to the position of the model data.

In Sample 4, the visualized data in the invention indicate the boundary (in the figure, the boundary is enclosed by the broken line) between the cool colors and the warm colors, more clearly than the example of the Hilbert transform.

In Sample 5, the visualized data in the invention indicate the boundary between the cool colors and the warm colors, more correctly than the example of the Hilbert transform. In the visualized data obtained by the Hilbert transform, the influence of noises appears in the whole area, and it cannot be said that also the width of the excitation interval is clearly indicated.

In Sample 6, non-existent swivel centers (the star symbols 76) are caused to appear due to the influence of noises in the visualized data obtained by the Hilbert transform, but the influence of noises does not particularly appear in the invention.

Embodiment 2

Next, Embodiment 2 will be described. Hereinafter, components which are identical with those of Embodiment 1 are denoted by the same reference numerals, and their description is omitted.

Figure 20:
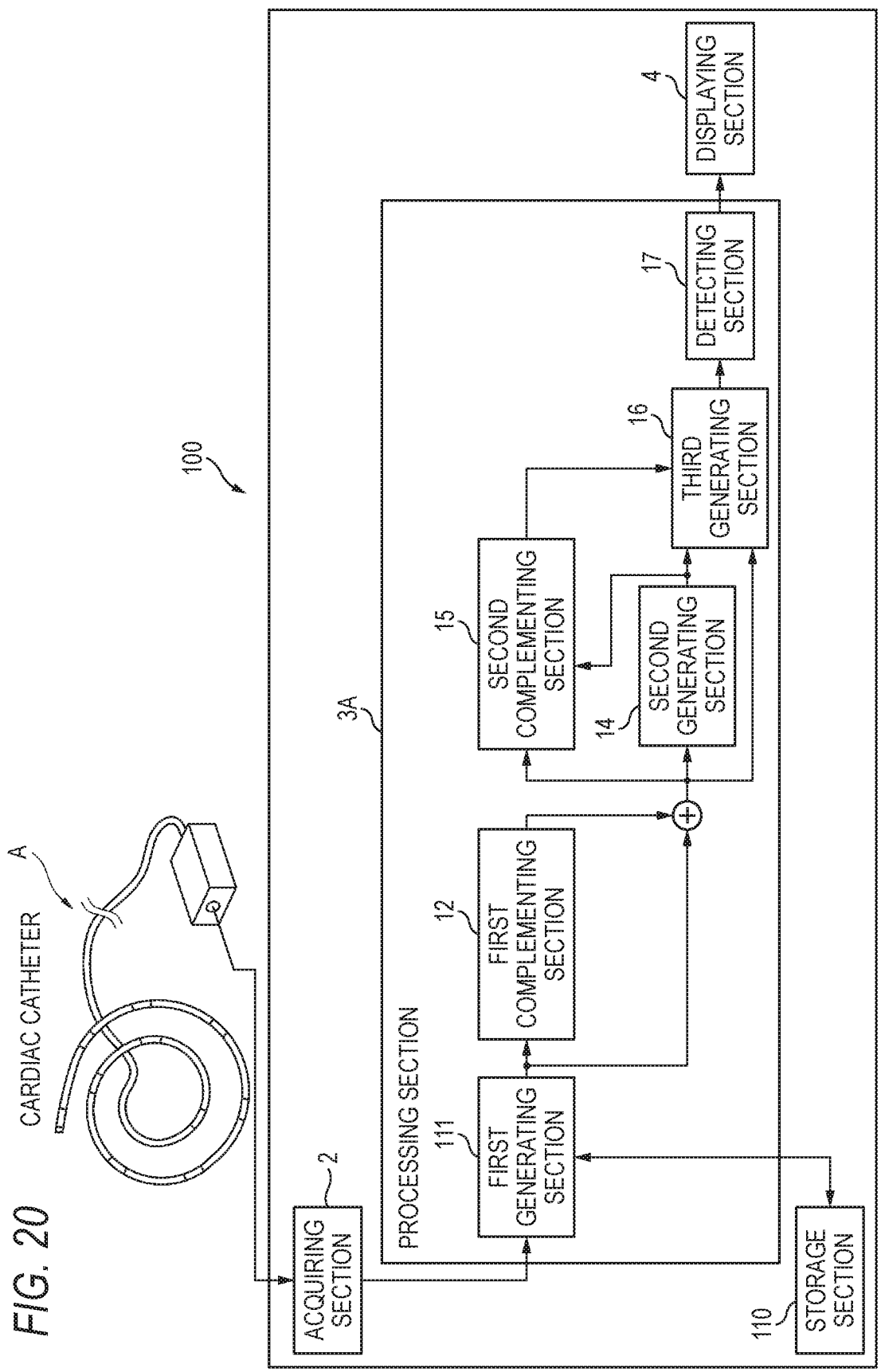
FIG. 20 is a diagram of a myocardial excitation complementation/visualization apparatus of Embodiment 2 of the invention.

As shown in FIG. 20, a myocardial excitation complementation/visualization apparatus 100 of Embodiment 2 includes the acquiring section 2, a processing section 3A, a storage section 110, and the displaying section 4. The processing section 3A includes a first generating section 111, the first complementing section 12, the second generating section 14, the second complementing section 15, the third generating section 16, and the detecting section 17.

Figure 21:
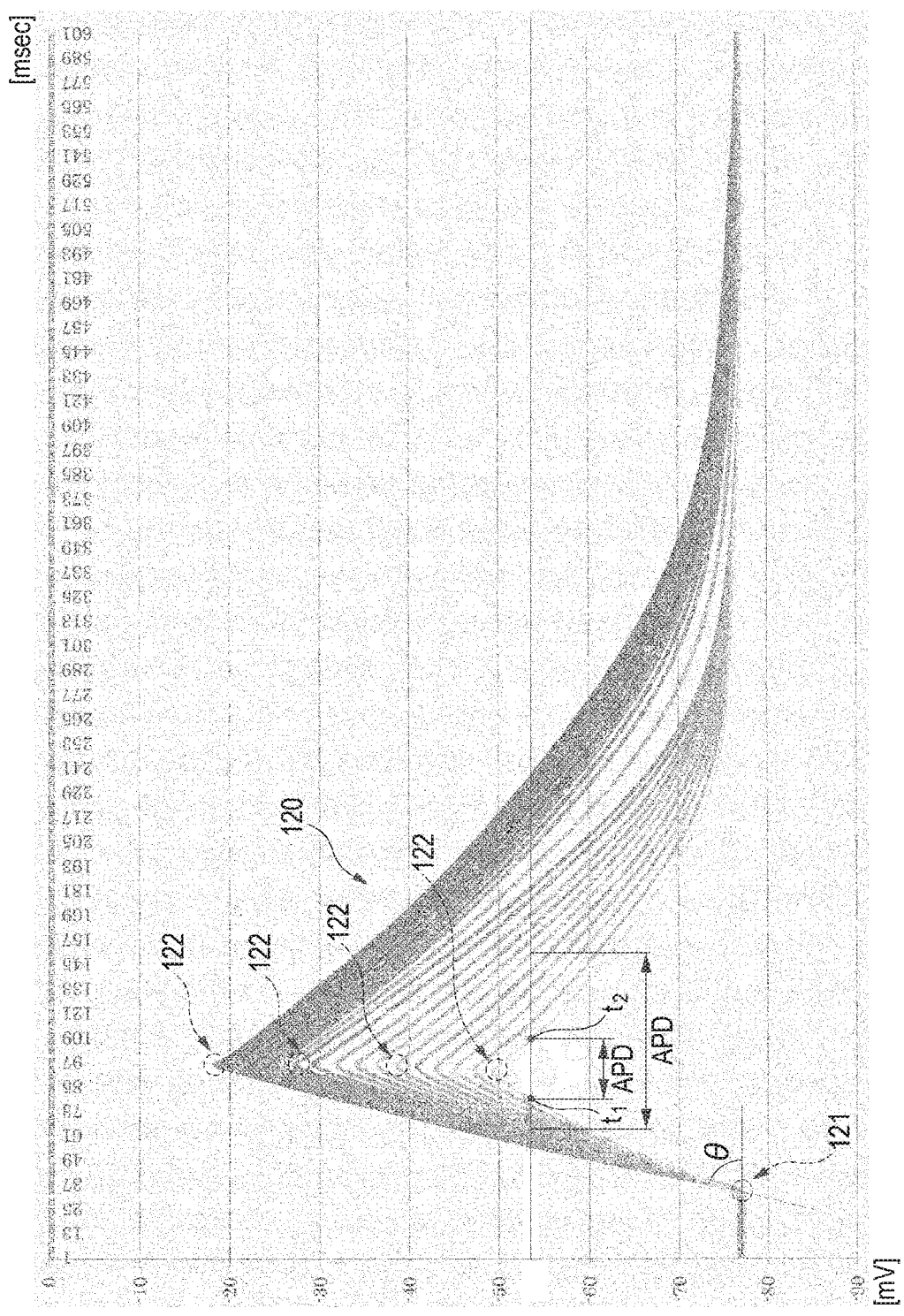
FIG. 21 is a view illustrating an action potential unit waveform for generating an action potential waveform.

The storage section 110 stores a plurality of action potential unit waveforms 120 which are as shown in, for example, FIG. 21, and which are previously generated. The action potential unit waveforms 120 are obtained by applying a temporal moving averaging process on an action potential waveform in the human atrial muscle under structural remodeling which is derived by computer simulation. The structural remodeling means a histoanatomical change which appears in a pathological condition of the atrial muscle. In each of the action potential unit waveforms 120, the rising from the start point 121 to the peak 122 is gentler (the rising angle θ is smaller) as compared with that in an ideal model (see FIG. 5A) of a unit waveform contained in the action potential waveforms in the myocardium. The storage section 110 is connected to the first generating section 111.

The first generating section 111 generates the pseudo action potential waveform 25 by using the action potential unit waveform 120 with respect to each of the plurality of intracardiac electrocardiograms which are acquired by the acquiring section 2. In the following description of Embodiment 2, a pseudo action potential waveform 25 is also referred to simply as an action potential waveform 25.

With respect to each of the action potential waveforms output from the first generating section 111 and the first complementing section 12, the second generating section 14 generates a shifted waveform which is shifted in time phase by a predetermined time from the action potential waveform.

The third generating section 16 prepares a phase portrait based on the action potential waveforms output from the first generating section 111 and the first complementing section 12, the shifted waveforms output from the second generating section 14, and the action potential waveforms and shifted waveforms output from the second complementing section 15. Moreover, the third generating section 16 calculates the phase based on the phase portrait, and generates visualized data (phase map) indicating the state of excitation in the myocardium.

The acquiring section 2, the first complementing section 12, the second complementing section 15, the detecting section 17, and the displaying section 4 are configured in a same or similar manner as the respective sections in Embodiment 1 described above.

Next, the operation of the myocardial excitation complementation/visualization apparatus 100 will be described.

The operation which is performed until the intracardiac electrocardiogram waveforms 21a to 21j recorded by the cardiac catheter A are placed respectively on the grids 23 is similar to that which is performed before and including the description of FIG. 3B in Embodiment 1 described above.

With respect to the recorded intracardiac electrocardiogram waveforms 21a to 21j, thereafter, the first generating section 11 generates the action potential waveforms 25 by using the action potential unit waveforms 120.

Figure 22:
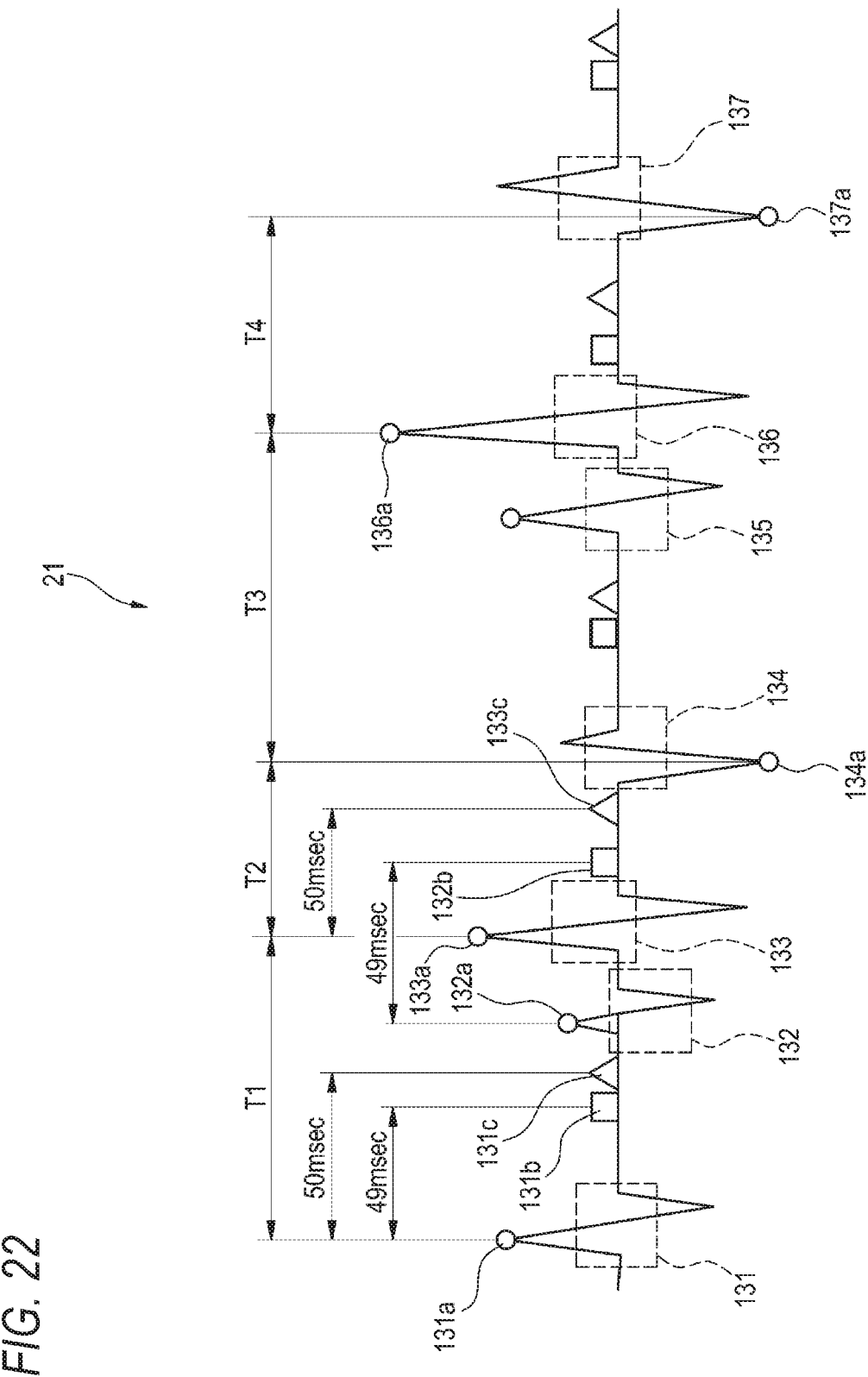
FIG. 22 is a view illustrating a procedure of detecting the waveform of myocardial excitation from an intracardiac electrocardiogram waveform.

In order to generate the action potential waveforms 25, as shown in FIG. 22, for example, the first generating section 11 first detects beats satisfying predetermined conditions, as candidate waveforms of myocardial excitation, from the recorded intracardiac electrocardiogram waveforms 21. Specifically, beats which satisfy conditions that, for example, the lateral width w is 10 msec or shorter, and the vertical width h is 0.1 mV or higher are detected (with respect to the lateral width w and the vertical width h, see FIG. 5C). In the case of the intracardiac electrocardiogram waveform 21 shown in FIG. 22, as beats satisfying the conditions, seven beats contained in the broken-line rectangles 131 to 137 are detected as candidate waveforms of myocardial excitation.

Then, the first generating section 11 further detects beats satisfying predetermined conditions as the waveform of myocardial excitation, from the detected candidate waveforms of myocardial excitation. With reference to the candidate waveforms of myocardial excitation, specifically, the first generating section 11 sets a search time period when another candidate waveform of myocardial excitation is searched, and a search exclusion time period when another candidate waveform of myocardial excitation is not searched. In this case, the search time period (for example, 49 msec) is set to a time period which is shorter than the search exclusion time period (for example, 50 msec).

As shown in FIG. 22, the first generating section 11 first detects, in the intracardiac electrocardiogram waveform 21, a beat which is contained in the broken-line rectangle 131, as a candidate waveform of myocardial excitation. The first generating section 11 searches whether or not another candidate waveform of myocardial excitation (a waveform contained in the broken-line rectangle) exists between the peak (the circle symbol 131a) of the detected candidate waveform of myocardial excitation, and the square symbol 131b after elapse of the search time period (49 msec). In the example, another candidate waveform of myocardial excitation does not exist in the search time period. In the example, therefore, the beat contained in the broken-line rectangle 131 is detected as the initial waveform of myocardial excitation. The first generating section 11 sets the time period between the peak (the circle symbol 131a) of the detected waveform of myocardial excitation, and the triangle symbol 131c after elapse of 50 msec, as the detection exclusion time period when another candidate waveform of myocardial excitation is not detected.

After the detection exclusion time period (after and including the triangle symbol 131c), the first generating section 11 detects a beat contained in a broken-line rectangle 132 as the next candidate waveform of myocardial excitation. Similarly with the above-described search, the first generating section 11 searches whether or not another candidate waveform of myocardial excitation exists between the peak (the circle symbol 132a) of the detected candidate waveform of myocardial excitation, and the square symbol 132b after elapse of the search time period. In the case of the example, a beat contained in a broken-line rectangle 133 is detected as another candidate waveform of myocardial excitation. The first generating section 11 compares the amplitudes (P-P values) of the two detected candidate waveforms of myocardial excitation (the beats contained in the broken-line rectangles 132, 133) with each other, and detects the candidate waveform having the larger amplitude, as the waveform of myocardial excitation. In the example, the beat contained in the broken-line rectangle 133 is detected as the waveform of myocardial excitation. The first generating section 11 sets the time period between the peak (the circle symbol 133a) of the detected waveform of myocardial excitation, and the triangle symbol 133c after elapse of 50 msec, as the detection exclusion time period in a manner similar to the above. The beat in the broken-line rectangle 132 which is not detected as the waveform of myocardial excitation is eliminated from waveforms for generating the action potential waveform 25.

When the above-described detecting process is repeated, in the intracardiac electrocardiogram waveforms 21 shown in FIG. 22, beats contained in the broken-line rectangles 131, 133, 134, 136, 137 are detected as waveforms of myocardial excitation.

Then, the first generating section 11 detects the time intervals between the detected waveforms (between the unit waveforms) of myocardial excitation. Specifically, the time interval T1 between the peak (the circle symbol 131a) of the beat contained in the broken-line rectangle 131, and the peak (the circle symbol 133a) of the beat contained in the broken-line rectangle 133 is detected. Similarly, the time interval T2 between the circle symbol 133a and the circle symbol 134a, the time interval T3 between the circle symbol 134a and the circle symbol 136a, and the time interval T4 between the circle symbol 136a and the circle symbol 137a are detected.

When the action potential waveforms 25 are to be generated by using the action potential unit waveforms 120, calculations are performed under the assumption that the detected time intervals T1 to T4 between the waveforms of myocardial excitation correspond to unit waveforms (hereinafter, referred to as unit action potential waveforms) CL1 to CL4 contained in the action potential waveforms 25 to be generated, respectively.

Figure 23:
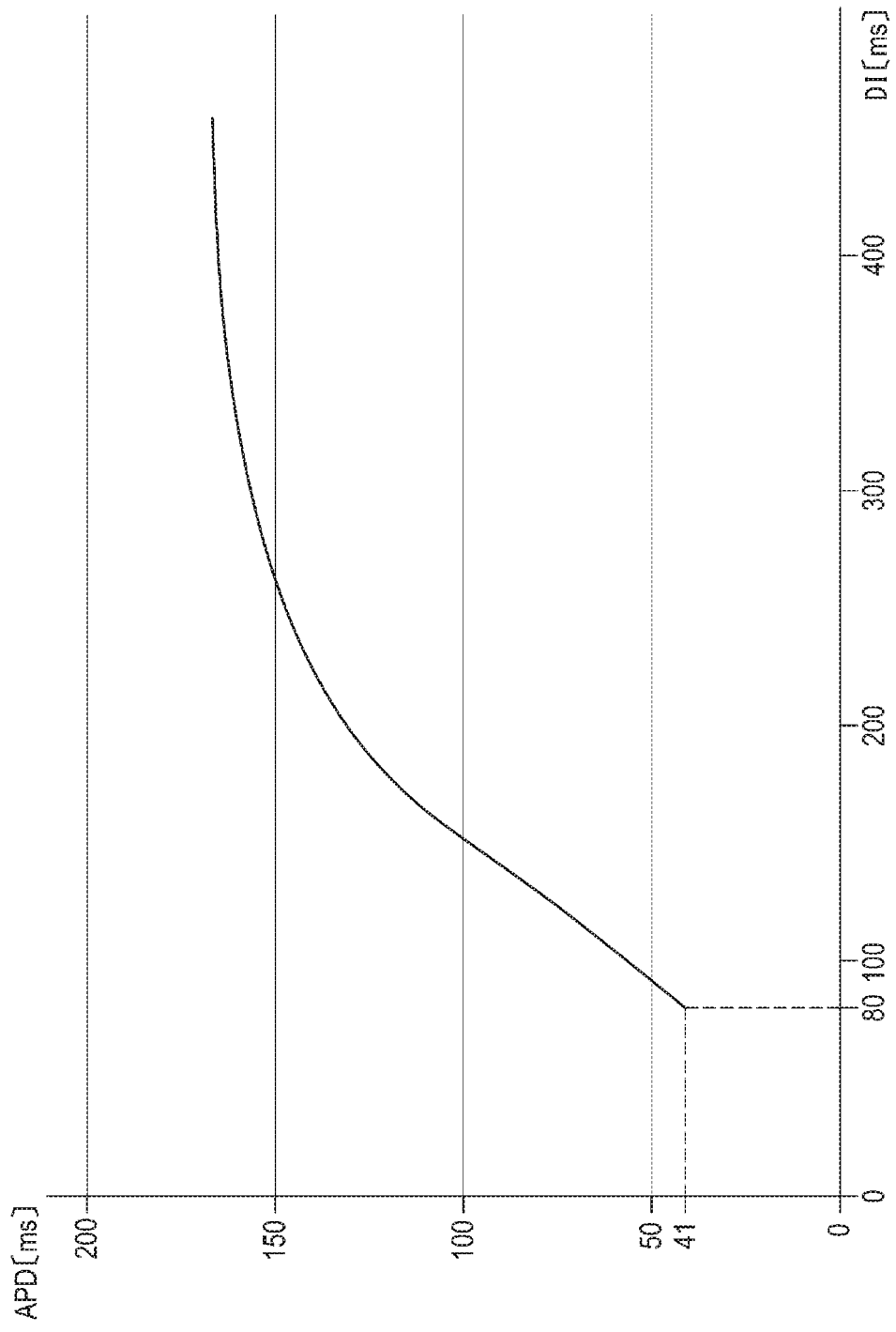
FIG. 23 is a graph illustrating relationships between a diastolic interval and action potential duration of an action potential unit waveform.

The first generating section 11 applies the shortest APD (41 msec) shown in the graph of FIG. 23, as the APD value of the unit action potential waveform which is generated with respect to the initial waveform of myocardial excitation (the beat contained in the broken-line rectangle 131). The first generating section 11 subtracts the shortest APD from the CL1 (T1) to obtain the value of the DI1 (DI1=CL1− shortest APD), and obtains the value of the APD with respect to the obtained value of the DI1 from the graph of FIG. 23. The obtained value of the APD is the value of the APD2 of the unit action potential waveform which is generated with respect to the second waveform of myocardial excitation (the beat contained in the broken-line rectangle 133).

Similarly, the values of the APDs (APD3, APD4, etc.) of unit action potential waveforms which are generated with respect to the third and subsequent waveforms of myocardial excitation are obtained.

Based on the obtained values of the APDs, then, the first generating section 11 selects action potential unit waveforms which are to be used in the production of the action potential waveforms 25, from the action potential unit waveforms 120 shown in FIG. 21. In each of the action potential unit waveforms 120 of FIG. 21, specifically, the time interval between two points (for example, between $t_1$ and $t_2$) indicating −53 mV is set as the value of the APD of the action potential unit waveform 120, and action potential unit waveforms 120 having the value of the APD which is close to the thus obtained values of the APDs (APD1, APD2, . . . ) are sequentially selected.

Figure 24:
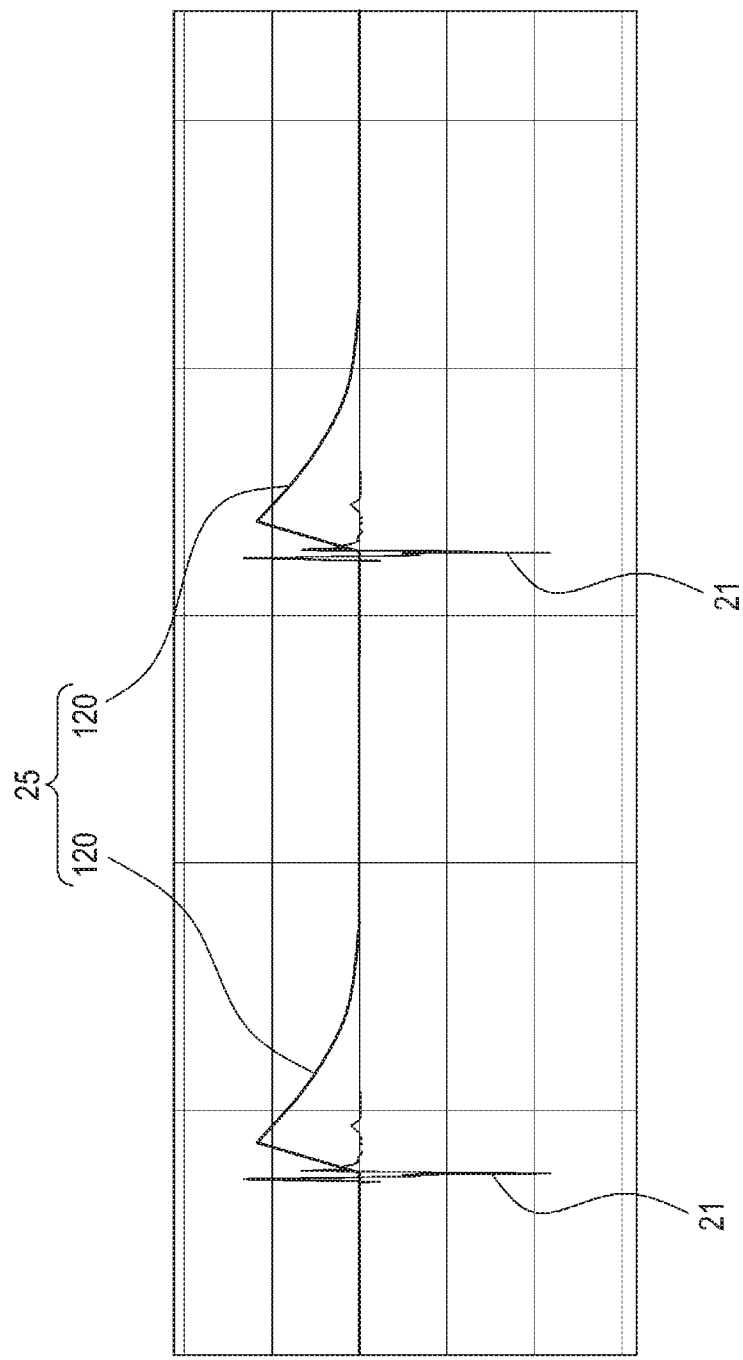
FIG. 24 is a view illustrating an intracardiac electrocardiogram waveform to which an action potential unit waveform is applied.
Figure 25:
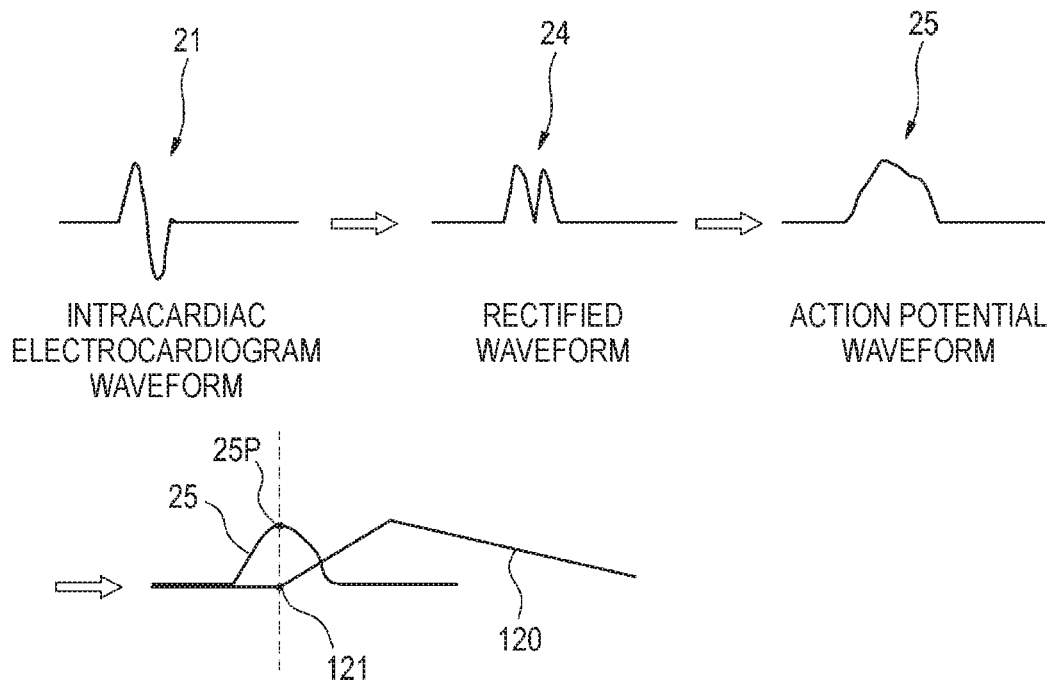
FIG. 25 is a view illustrating a display position of an action potential unit waveform with respect to an intracardiac electrocardiogram waveform.

The selected action potential unit waveforms 120 are displayed as waveforms for generating the action potential waveforms 25, correspondingly to the intracardiac electrocardiogram waveform 21 as shown in FIG. 24. The display position of each of the action potential unit waveforms 120 relative to the intracardiac electrocardiogram waveform 21 is as shown in FIG. 25. When the intracardiac electrocardiogram waveform 21 is rectified to prepare the rectified waveform 24, and a moving averaging prepare is applied to the rectified waveform 24 to prepare the action potential waveform 25, for example, the time phase of the peak 25P of the action potential waveform 25 is the position of the start point 121 of the action potential unit waveform 120.

Similarly, the first generating section 11 generates the action potential waveforms 25a to 25j with respect to the intracardiac electrocardiogram waveforms 21a to 21j.

In a similar manner as Embodiment 1 described above, then, the first complementing section 12 sets the positions of virtual electrodes, and interpolates the action potential waveform 25k and the like with respect to the set virtual electrodes.

In Embodiment 2, the action potential unit waveforms are used, and therefore the correction in which, as in Embodiment 1, the amplitudes of the action potential waveforms are equalized by the correcting section is not performed.

Then, the second generating section 14 calculates the mean APD of the values of the APDs (APD3, APD4, etc.) of the unit action potential waveforms, and, similarly with Embodiment 1 described above, generates the shifted waveforms 40a to 40k. The action potential waveforms 25a to 25k and the shifted waveforms 40a to 40k are placed on the grids 23 at the positions where the electrodes and the virtual electrodes are disposed, respectively (see FIG. 10B).

The processing operations which are performed in the following steps in the second complementing section 15, the third generating section 16, the detecting section 17, and the displaying section 4 are similar to those in Embodiment 1 described above.

Figure 26:
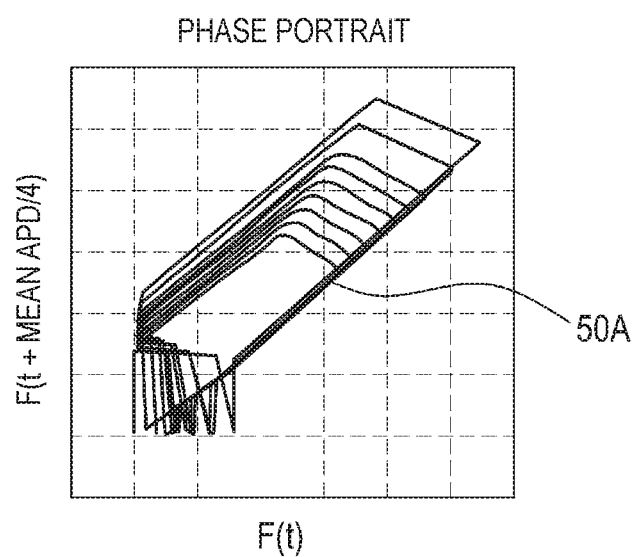
FIG. 26 is a phase portrait which is drawn based on an action potential unit waveform

According to the above-described myocardial excitation complementation/visualization apparatus 100, similarly with Embodiment 1, phase portraits 50A (see FIG. 26) and visualized data are prepared based on the action potential waveforms and the shifted waveforms, and therefore the computation amount can be remarkably suppressed. The pseudo action potential waveforms 25 are generated by using the action potential unit waveforms 120 that are previously generated by computer simulation. Therefore, it is possible to suppress influences due to far field potentials and noises which may be contained in the intracardiac electrocardiogram waveforms 21, and the state of excitation in the myocardium can be accurately reflected in the visualized data. According to the configuration, the visualized data can be continuously prepared from the intracardiac electrocardiograms 21 recorded by the cardiac catheter A, and the state of excitation in the myocardium can be accurately displayed in real time.

Moreover, the action potential unit waveforms 120 for generating the action potential waveforms 25 are selected based on the relationship of the DI and APD in the ideal model of a unit waveform contained in the action potential waveforms in the myocardium. Therefore, it is possible to further suppress influences due to far field potentials and noises which may be contained in the intracardiac electrocardiogram waveforms 21, and the state of excitation in the myocardium can be accurately reflected in the visualized data.

Moreover, the time phases of the positions of the peaks of the action potential unit waveforms 120 which are previously prepared are identical with one another. Even when a correcting process of equalizing the heights of the action potential unit waveforms is not performed, therefore, the positions of the centers can be easily determined in the case where the phase portraits 50A are to be prepared. Consequently, the positions of the centers of the samples 51 in the phase portraits 50A can be equalized with one another, and, even when the Hilbert transform is not used, the state of excitation in the myocardium can be accurately reflected in the visualized data.

Moreover, the use of a waveform which is obtained by applying a moving averaging process on an action potential waveform in the human atrial muscle under structural remodeling which is derived by computer simulation can prevent the angle information of each of the samples 51 from the center portion of the phase portrait 50A from being biased. When visualized data are to be continuously prepared, and the state of excitation in the myocardium is to be displayed in real time, therefore, the state of excitation can be prevented from being instantly changed, and can transition smoothly and continuously, so that a change of the state of excitation in the myocardium can be easily observed.

In addition, the embodiment achieves similar effects as those of Embodiment 1 with respect also to the advantages such as that an FFT and an IFFT are not required to be performed, the indication of a portion where the excitation rests, in the rear surface of the action potential waveform, the drawing of the isochrone, the definition of the colors of the phase portraits, and the detection of a phase singularity.

The invention is not limited to the above-described embodiments, and may be adequately subjected to modification, improvement, and the like. In addition, the materials, shapes, dimensions, numerical values, forms, numbers, placement places, and the like of the components of the above-described embodiments are arbitrary and not limited insofar as the invention is achieved.

Although the above-described embodiments have the displaying section 4 which enables a change of the state of excitation to be observed based on the visualized data, for example, an apparatus having a configuration which does not have a displaying section (displaying function), and which has only a detecting section (detecting function) that detects a phase singularity, such as a myocardial excitation detection apparatus may be employed.

Although the invention has been described in detail and with reference to the specific embodiments, it is obvious to a person skilled in the art that various changes and modifications can be made without departing from the spirit and scope of the invention.

The application is based on Japanese Patent Application No. 2015-70249 filed on Mar. 30, 2015, and its disclosure is incorporated herein by reference.

What is claimed is:

1. A myocardial analysis apparatus comprising:
an acquiring section that acquires intracardiac electrocardiograms of a subject, the intracardiac electrocardiograms being recorded by a recording unit having a plurality of electrodes;
a processing section that performs a computation for completing and visualizing a state of excitation in a myocardium of the subject based on the intracardiac electrocardiograms; and
a displaying section that displays the state of excitation in the myocardium of the subject based on an output of the processing section, wherein the processing section includes:
a first generating section which, with respect to each of the plurality of intracardiac electrocardiograms that are recorded by the plurality of electrodes of the recording unit, generates a pseudo action potential waveform;
a correcting section which performs a correction for equalizing amplitudes of unit waveforms contained in the action potential waveforms;
a second generating section which, with respect to each of the action potential waveforms corrected by the correcting section, generates a shifted waveform that is different in time phase from the action potential waveform; and
a third generating section which prepares a phase portrait based on each of the action potential waveforms corrected by the correcting section, and the shifted waveform corresponding to the action potential waveform, and which generates visualized data indicating the state of excitation in the myocardium of the subject, based on the phase portraits, and
the displaying section displays a change of the state of excitation in the myocardium of the subject based on the visualized data.

2. The myocardial analysis apparatus according to claim 1, wherein the shifted waveform is a waveform which is different in time phase by N+(¼) of a mean action potential duration from the action potential waveform, and
N is 0 or a positive integer.

3. The myocardial analysis apparatus according to claim 1, wherein, when the pseudo action potential waveform is to be generated, the first generating section detects a unit waveform in the pseudo action potential waveform by using a shortest cycle length which is obtained by adding a shortest diastolic interval and shortest action potential duration in an ideal model of a unit waveform contained in the action potential waveform of the myocardium.

4. The myocardial analysis apparatus according to claim 1, wherein the correcting section performs the correction based on relationships between a diastolic interval and action potential duration in an ideal model of a unit waveform contained in the action potential waveform of the myocardium.

5. The myocardial analysis apparatus according to claim 1, wherein the processing section includes:
a first complementing section which defines a virtual electrode at a position which is in the myocardium of the subject, and in which the electrodes of the recording unit are not placed, and that interpolates a pseudo action potential waveform with respect to the virtual electrode, based on the action potential waveforms generated with respect to electrodes surrounding the virtual electrode; and
a second complementing section which interpolates the pseudo action potential waveform and the shifted waveform by using a spatial interpolation technique with respect to positions which are in the myocardium of the subject, and in which the electrodes of the recording unit and the virtual electrode are not placed.

6. The myocardial analysis apparatus according to claim 1, wherein, when visualized data indicating the state of excitation in the myocardium of the subject are to be generated based on the phase portrait, in a unit waveform contained in the action potential waveform, the third generating section defines a portion where the action potential exceeds a center of the phase portrait with a warm color, and a portion where the action potential is lower than the center with a cool color.

7. The myocardial analysis apparatus according to claim 1, wherein the processing section has a detecting section which extracts a first grid set that is configured by a predetermined number of grids, from the visualized data, and which detects a center of the first grid set as a phase singularity in a case where a total of color differences between adjacent grids in the first grid set is equal to or larger than a predetermined value, and all of predetermined colors are contained in a second grid set that is centered on the first grid set, and that is configured by grids a number of which is larger than a number of the grids in the first grid set.

8. A myocardial analysis apparatus comprising:
an acquiring section that acquires intracardiac electrocardiograms of a subject, the intracardiac electrocardiograms being recorded by a recording unit having a plurality of electrodes;
a processing section that performs a computation for completing and visualizing a state of excitation in a myocardium of the subject based on the intracardiac electrocardiograms;
a displaying section that displays state of excitation in a myocardium of the subject based on an output of the processing section; and
a storage section that stores a plurality of action potential unit waveforms that are previously generated by computer simulation,
wherein the processing section includes:
a first generating section which, with respect to each of the plurality of intracardiac electrocardiograms that are recorded by the plurality of electrodes of the recording unit, generates a pseudo action potential waveform by using the action potential unit waveforms;
a second generating section which, with respect to each of the action potential waveforms, generates a shifted waveform that is different in time phase from the action potential waveform; and
a third generating section which prepares a phase portrait based on each of the action potential waveforms and the shifted waveform corresponding to the action potential waveform, and which generates visualized data indicating the state of excitation in the myocardium of the subject, based on the phase portraits, and
the displaying section displays a change of the state of excitation in the myocardium of the subject based on the visualized data.

9. The myocardial analysis apparatus according to claim 8, wherein the shifted waveform is a waveform which is different in time phase by N+(¼) of a mean action potential duration from the action potential waveform, and
N is 0 or a positive integer.

10. The myocardial analysis apparatus according to claim 8, wherein the first generating section detects time intervals between the unit waveforms contained in the intracardiac electrocardiogram, and sequentially selects the action potential unit waveforms which are to be used in the production of the pseudo action potential waveform, based on relationships between a diastolic interval and action potential duration in an ideal model of a unit waveform contained in the action potential waveform of the myocardium.

11. The myocardial analysis apparatus according to claim 8, wherein
The processing section includes:
a first complementing section that defines a virtual electrode at a position which is in the myocardium of the subject, and in which the electrodes of the recording unit are not placed, and that interpolates a pseudo action potential waveform with respect to the virtual electrode, based on the action potential waveforms generated with respect to electrodes surrounding the virtual electrode; and
a second complementing section that interpolates the pseudo action potential waveform and the shifted waveform by using a spatial interpolation technique with respect to positions which are in the myocardium of the subject, and in which the electrodes of the recording unit and the virtual electrode are not placed.

12. The myocardial analysis apparatus according to claim 8, wherein, when visualized data indicating the state of excitation in the myocardium of the subject are to be generated based on the phase portrait, in an action potential unit waveforms contained in the action potential waveform, the third generating section defines a portion where the action potential exceeds a center of the phase portrait with a warm color, and a portion where the action potential is lower than the center with a cool color.

13. The myocardial analysis apparatus according to claim 8, wherein the processing section has a detecting section which extracts a first grid set that is configured by a predetermined number of grids, from the visualized data, and which detects a center of the first grid set as a phase singularity in a case where a total of color differences between adjacent grids in the first grid set is equal to or larger than a predetermined value, and all of predetermined colors are contained in a second grid set that is centered on the first grid set, and that is configured by grids a number of which is larger than a number of the grids in the first grid set.

14. The myocardial analysis apparatus according to claim 8, wherein, in each of the action potential unit waveforms, rising from a start point to a peak is gentler as compared with an ideal model of a unit waveform contained in the action potential waveforms in the myocardium.

15. A myocardial excitation detection apparatus comprising:
an acquiring section that acquires intracardiac electrocardiograms of a subject, the intracardiac electrocardiograms being recorded by a recording unit having a plurality of electrodes; and
a processing section that performs a computation for completing and visualizing a state of excitation in a myocardium of the subject based on the intracardiac electrocardiograms,
wherein the processing section includes:
a first generating section which, with respect to each of the plurality of intracardiac electrocardiograms that are recorded by the plurality of electrodes of the recording unit, generates a pseudo action potential waveform;
a second generating section which, with respect to each of the action potential waveforms, generates a shifted waveform that is different in time phase from the action potential waveform;
a third generating section which prepares a phase portrait based on each of the action potential waveforms and the shifted waveform corresponding to the action potential waveform, and which generates visualized data indicating the state of excitation in the myocardium of the subject, based on the phase portraits; and
a detecting section which extracts a first grid set that is configured by a predetermined number of grids, from the visualized data, and which detects a center of the first grid set as a phase singularity in a case where a total of color differences between adjacent grids in the first grid set is equal to or larger than a predetermined value, and all of predetermined colors are contained in a second grid set that is centered on the first grid set, and that is configured by grids a number of which is larger than a number of the grids in the first grid set.

16. The myocardial excitation detection apparatus according to claim 15, wherein the phase singularity is a rotor of fibrillation on an atrial wall.

17. The myocardial excitation detection apparatus according to claim 15, wherein the second grid set includes the first grid set.

18. The myocardial excitation detection apparatus according to claim 15, wherein the detecting section calculates a color difference for each combination of adjacent two grids in the first grid set.

* * * * *